(12) United States Patent
Blackburn et al.

(10) Patent No.: US 6,576,619 B2
(45) Date of Patent: *Jun. 10, 2003

(54) ORALLY ACTIVE A1 ADENOSINE RECEPTOR AGONISTS

(75) Inventors: Brent K. Blackburn, Los Altos, CA (US); Chris Melville, Palo Alto, CA (US); Jeff A. Zablocki, Mountain View, CA (US); Venkata P. Palle, Mountain View, CA (US); Elfaith O. Elzein, Freemont, CA (US); Lisa Wang, Burlingame, CA (US)

(73) Assignee: CV Therapeutics, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,523

(22) Filed: May 24, 1999

(65) Prior Publication Data

US 2002/0091099 A1 Jul. 11, 2002

(51) Int. Cl.$^7$ .................. A61K 31/70; C07H 19/167

(52) U.S. Cl. .................. 514/46; 536/27.6; 536/27.62

(58) Field of Search .................. 514/46; 536/27.62, 536/27.6

(56) References Cited

U.S. PATENT DOCUMENTS

| | | | |
|---|---|---|---|
| 3,998,953 A | 12/1976 | Konz et al. | 424/253 |
| 4,364,922 A | 12/1982 | Berne et al. | 424/9 |
| 4,464,361 A | * 8/1984 | Ohki et al. | 514/46 |
| 4,713,455 A | 12/1987 | Furrer et al. | 544/267 |
| 4,954,504 A | 9/1990 | Chen et al. | 514/265 |
| 4,980,379 A | 12/1990 | Belardinellli et al. | 514/821 |
| 5,288,721 A | 2/1994 | Klein et al. | 514/263 |
| 5,446,046 A | 8/1995 | Belardinelli et al. | 514/263 |
| 5,773,423 A | 6/1998 | Jacobsen et al. | 514/45 |
| 5,789,416 A | * 8/1998 | Lum et al. | 514/261 |

FOREIGN PATENT DOCUMENTS

| | | |
|---|---|---|
| DE | 4205306 A1 | 2/1992 |
| EP | 0 062 921 | 10/1982 |
| EP | 0 179 630 A2 | 4/1986 |
| EP | 0 181 109 A2 | 5/1986 |
| EP | 0374 808 A2 | 12/1989 |
| EP | 0 402 752 | 12/1990 |
| EP | 0 415 456 A2 | 3/1991 |
| WO | WO 88/03148 | 5/1988 |
| WO | WO 92/00297 | 6/1990 |
| WO | WO 90/09178 | 8/1990 |
| WO | WO 94/16702 | 1/1993 |
| WO | WO 93/08206 | 4/1993 |
| WO | WO 98/08855 | 3/1998 |
| WO | 9924450 | * 5/1999 |
| WO | 9924451 | * 5/1999 |

OTHER PUBLICATIONS

Jacobsen et al., "Adenosine Receptors: Pharmacology, Structure–Activity Relationships, and Therapeutic Potential," *Journal of Medicinal Chemistry*, 35(3), 407–422 (Feb. 7, 1992).*

Odawara et al., "Relaxations of Isolated Rabbit Coronary Artery by Purine Derivatives: $A_2$–Adenosine Receptors," *Journal of Cardiovascular Pharmacology*, 8(3), 567–573 (1986); *Chemical Abstracts*, 105(9), page 88, Abstract No. 72837n (Sep. 1, 1986); only abstract supplied (new legible copy made from CA).*

Knutsen et al., "The Synthesis and Biochemical Evaluation of New $A_1$ Selective Adenosine Receptor Agonists Containing 6–Hydrazinopurine Moieties," *Bioorganic & Medicinal Chemistry Letters*, 3(12), 2661–2666 (Dec. 1993); *Chemical Abstracts*, 121(3), p. 18, Abstract No. 26237s (Jul. 18, 1994); abstract supplied by applicant (new legible copy made from CA).*

Deparade et al., "The Binding of Spin–Labeled Derivatives of NAD+ and Its Structural Components to Pig Skeletal Muscle Lactate Dehydrogenase," *Biochimica et Biophysica Acta*, 568(1), 177–182 (May 10, 1979).*

Wenzel et al., "The Synthesis of Spin–Labeled Derivatives of NAD+ and Its Structural Components and Their Binding To Lactate Dehydrogenase," *Biochimica et Biophysica Acta*, 452(1), 292–301 (Nov. 8, 1976).*

(List continued on next page.)

*Primary Examiner*—Samuel Barts
*Assistant Examiner*—Lawrence E. Crane
(74) *Attorney, Agent, or Firm*—McDonnell Boehnen Hulbert & Berghoff

(57) ABSTRACT

Esters of $N^6$-oxa, thia, thioxa and azacycloalkyl substituted adenosine derivatives having the following formula;

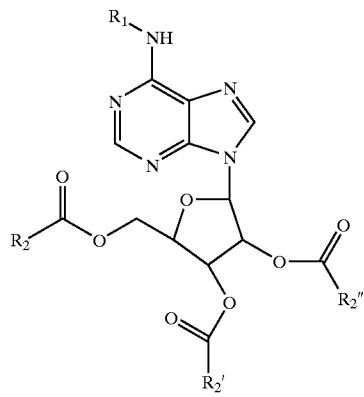

wherein the compounds are selective adenosine type 1 receptor agonists that are useful for the treatment cardiovascular diseases and central nervous system disorders.

22 Claims, 5 Drawing Sheets

OTHER PUBLICATIONS

De Zwart et al., "The Functional Screening of Adenosine Analogs at the Adenosine $A_{2B}$ Receptor: A Search for Potent Agonists," *Nucleosides Nucleotides, 17*(6), 969–985 (1998); *Chemical Abstracts, 129*(7), p. 23, Abstract No. 75990p (Aug. 17, 1998); only Abstract supplied.*

Munter et al., "Identification of Adducts Formed in Reaction of Adenosine with 3–Chloro–4–methyl–5–hydroxy–2(5H)–furanone, a Bacterial Mutagen Present in Chlorine Disinfected Drinking Water," *Chemical Research in Toxicology, 9*(4), 703–708 (Jun. 1996).*

Chelsky et al., "Stereochemical Course of the Adenosine Triphosphate Phosphoribosyltransferase Reaction in Histidine Biosynthesis," *Journal of Biological Chemistry, 250*(14), 5669–5673 (Jul. 25, 1975).*

Hutchinson et al., "Adenosine Receptor Ligands with Oxygenated $N^6$–Substituents," *Bioorganic & Medicinal Chemistry Letters, 9*(7), 933–936 (Apr. 5, 1999).*

Ha et al., "New Base–Altered Adenosine Analogues: Synthesis and Affinity at Adenosine $A_1$ and $A_{2A}$ Receptors", *Bioorganic & Medicinal Chemistry Letters,* vol. 7, pp. 3085–3090 (1997).

Kosugi et al., "Synthesis of $N^6$–(2–Oxopyrrolidin–5–YL) Adenosine Derivatives", *Heterocycles,* vol. 24, pp. 625–628 (1986).

Nagasaka et al., "5–Acetoxy–2–pyrrolidinone as a precursor for N–acylimminium ion", *Heterocycles,* vol. 20, pp. 985–990 (1983).

L. Belardinelli, *Drug Development Research,* 28, pp. 263–267 (1993).

L. Belardinelli, et al, *Pace,.* vol., 14, pp. 1672–1680 (1991) (Nov. 1991, part 1).

L. Belardineilli, et al, *Progress in Cardiovascular Disease,* vol. XXXII, No. 1 (Jul./Aug.), pp. 73–97 (1989).

L. Belardinelli, et al, *Cardiac Electrophysiology of Adenosine,* pp. 327–339 (1990) (Aug. 1990).

R. Olsson, et al, *The American Physiological Society,* vol. 70, pp. 761–782 (1990) (Jul. 1990).

Fleysher, *J. Med. Chem,* vol. 15, pp. 187–191 (1972).

* cited by examiner

ORALLY ACTIVE A1 ADENOSINE RECEPTOR AGONISTS

BACKGROUND OF THE INVENTION

1. Field of Invention

There is provided exceptionally stable and useful pro-drugs that are esters of $N^6$-oxa, thia, thioxa and azacycloalkyl substituted adenosine derivatives that are selective adenosine type 1 receptor agonists, and as such, are potentially useful agents for the treatment cardiovascular diseases and central nervous system disorders.

2. Description of the Art

There are at least two subtypes of adenosine receptors in the heart: $A_1$ and $A_2$. Each subtype effects different physiological functions. Stimulation of the $A_1$ adenosine receptor induces two distinct physiological responses. The first is the inhibition of the stimulatory effects of catecholamine. This effect is mediated via the inhibition of cyclic AMP synthesis. The second effect mediated by $A_1$ receptors is the slowing of the heart rate and impulse propagation through the AV node. The effect is independent of cAMP metabolism and is associated with $A_1$ adenosine receptor activation of the inwardly rectifying K+ channel. This effect is unique to the $A_1$ receptor; there is no role for the $A_2$ receptor in modulating the function of this channel. Stimulation of the adenosine $A_1$ receptor accordingly shortens the duration and decreases the amplitude of the action potential of AV nodal cells and subsequently prolongs the refractory period of the cells. The consequence of these effects is to limit the number of impulses conducted from the atria to the ventricles. This forms the basis of the clinical utility of $A_1$ receptor agonists for the treatment of supraventricular tachycardias, including atrial fibrillation, atrial flutter, and AV nodal re-entrant tachycardia.

The clinical utility of $A_1$ agonists therefore would be in the treatment of acute and chronic disorders of heart rhythm, especially those diseases characterized by rapid heart rate where the rate is driven by abnormalities in the atria. The disorders include but are not limited to atrial fibrillation, supra ventricular tachycardia and atrial flutter. Exposure to $A_1$ agonists causes a reduction in the heart rate and a regularization of the abnormal rhythm thereby restoring improved hemodynamic blood flow.

$A_1$ agonists, through their ability to inhibit the catecholamine induced increase in cAMP, should have beneficial effects in the failing heart where increased sympathetic tone causing enhanced cAMP has been associated with increased likelihood of ventricular arrhythmias and sudden death.

There are a number of A1 agonists disclosed in the prior art. However, the agonists disclosed are generally disclosed in the forms that are useful in the mammalian body. Because the useful forms may not always be stable, soluble or they may have other properties that make their incorporation into therapeutic dosage forms difficult, it is often necessary to identify compositions that are more easily incorporated into therapeutic dosage forms in order to provide the desired therapeutic effect. Therefore, there remains a need for specific A1 agonists precursors or pro-drugs that are converted in the body into useful therapeutic compositions.

Often, useful compounds may be altered to pro-drug form such that the desired compound is created in the body of the patient as the result of the action of metabolic or other biochemical process on the pro-drug. Such pro-drug forms typically demonstrate little or no activity in vitro assays. Some examples of pro-drug forms include ketal, acetal, oxime, and hydrazone forms of compounds which contain ketone or aldehyde groups, especially where they occur in the R.sub.1 group of the compounds of this invention.

SUMMARY OF THE INVENTION

An object of this invention are novel pro-drugs of heterocyclic substituted adenosine derivatives.

Another object of this invention are pro-drugs of heterocyclic substituted adenosine derivatives that are converted in the mammalian body to become useful $A_1$ receptor agonists.

Still another object of this invention are pro-drugs of heterocyclic substituted adenosine derivatives that are useful for treating supraventricular tachycardias, including atrial fibrillation, atrial flutter, and AV nodal re-entrant tachycardia in mammals and especially humans.

A composition of matter having the formula

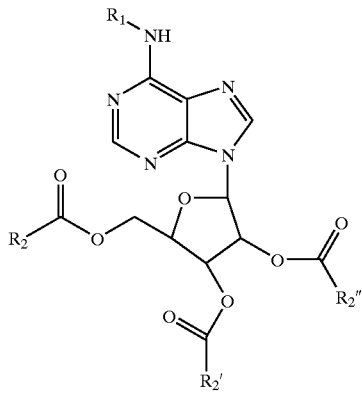

wherein $R_1$ is a monocyclic or polycyclic heterocyclic group containing from 3 to 15 atoms, at least one of which is selected from the group consisting of N, O, P and S—$(O)_{0-2}$ and wherein $R_1$ does not contain an epoxide group, and wherein $R_2$ $R_2'$, and $R_2''$ are independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$; wherein $R^{20}$ is a member selected from the group consisting of H, $C_{1-15}$ alkyl, $_{C2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is a member selected from the group consisting of $C_{1-15}$ alkyl, $_{C2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl.

In another embodiment, this invention is a method for stimulating coronary activity in a mammal experiencing a coronary electrical disorder that can be treated by stimulating an $A_1$ heart adenosine receptor by administering a therapeutically effective amount of the composition disclosed above to the mammal.

In still another embodiment, this invention is a pharmaceutical composition of matter comprising the composition of this invention and one or more pharmaceutical excipients.

DESCRIPTION OF THE CURRENT EMBODIMENT

Figure 1A:
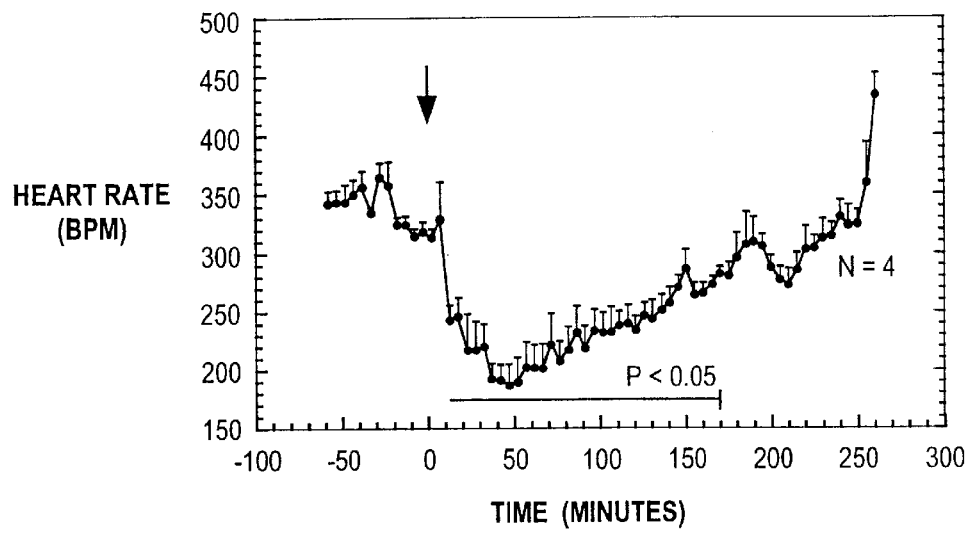
FIG. 1A is a plot of heart rate over time prior to and following administration of compound 2 of Example 1 to 4 rats in an oral gavage at a dose of 0.5 mg/kg.

A useful class of A1 agonists are those disclosed in U.S. Pat. No. 5,789,416 the specification of which is incorporated herein by reference. The bioactive '416 patent compositions have the following general formula:

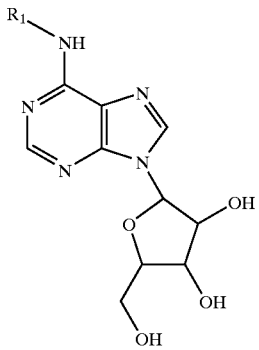

This invention includes pro-drugs of the above-identified A1 agonists. A pro-drug is a drug which has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxl groups. The modifications may be (1) ester or carbamate derivatives which may be cleaved by esterases or lipases, for example; (2) peptides which may be recognized by specific or non specific proteinase; or (3) derivatives that accumulate a site of action through membrane selection or a pro-drug form or modified pro-drug form, or any combination of (1) to (3) above. The preferred pro-drug compositions of this invention are modified to form esters and have the compositions described immediately below:

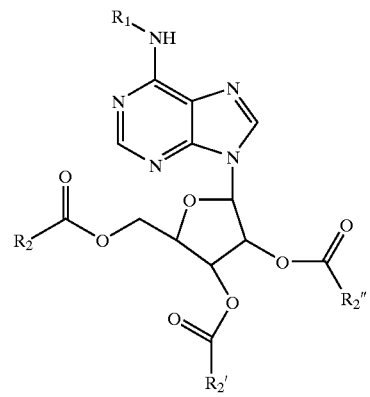

where $R_1$ is a cycloalkyl group, containing 3 to 15 atoms either monocyclic or polycyclic heterocyclic groups, at least one of which is a heteroatom selected from the group consisting of N, O, P, and S—$(O)_{0-2}$. $R_1$, in turn, may optionally be mono or polysubstituted with halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano. However, $R_1$ cannot contain an epoxy group.

$R_1$ is preferably a monocyclic, bicyclic, or tricyclic group containing from 3 to 15 atoms, at least one of which is selected from the group consisting of 0 or S—$(O)_{0-2}$ wherein $R_1$ may be mono or polysubstituted with one or more compounds selected from the group consisting of halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof.

A more preferred embodiment of $R_1$ is:

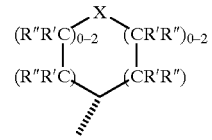

wherein R' and R" are individually selected from the group halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof and X is O, or S (—O)$_{0-2}$. Preferably, R', and R" are individually selected from the group hydrogen, lower alkyl, substituted lower alkyl, alkoxy, aryl, and substituted aryl. By "individually selected" it is meant that R' and R" may each be a different component, each may be the same component, e.g., hydrogen, or some of the components may be the same and some different. It is most preferred that when $R_1$ is the composition set forth above, that R' and R" are individually selected from the group H, lower alkyl, and substituted lower alkyl. R' and $R_1$" may also combine to form a single oxygen atom.

In an alternative embodiment, $R_1$ is selected from the group consisting of:

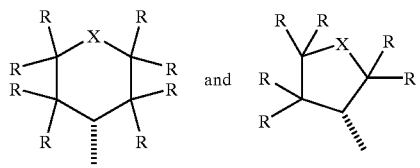

wherein each R may individually selected from the group consisting of H, lower alkyl, and substituted lower alkyl and wherein X is O, or S(—O)$_{0-2}$. In a most preferred embodiment, $R_1$ is selected from the group consisting of 3-tetrahydrofuranyl, 3-tetrahydrothiofuranyl, 4-pyranyl and 4-thiopyranyl.

$R_2$ $R_2$', and $R_2$" are each independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 2 or with 1 to 3 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$; wherein $R^{20}$ is a member selected from the group consisting of H, $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, $CF_3$, and heteroaryl.

Preferably $R_2$, $R_2$', and $R_2$" are each independently selected from the group consisting of $C_{1-6}$ alkyl, and aryl, which alkyl and aryl are optionally substituted with 1 to 2 substituents independently selected from the group of halo, $NO_2$, aryl, $CF_3$, CN, $OR^{20}$, $N(R^{20})_2$, $S(O)R^{22}$, $SO_2R^{22}$, $N(R^{20})_2$, and each optional aryl substituent is optionally substituted with halo, $NO_2$, alkyl, $CF_3$; wherein $R^{20}$ is a member selected from the group consisting of H, $C_{1-6}$ alkyl, and aryl, which alkyl and aryl are optionally substituted with 1 substituent independently selected from halo, alkyl, mono- or dialkylamino, CN, O—$C_{1-6}$ alkyl, $CF_3$; and $R^{22}$ is a member selected from the group consisting of $C_{1-6}$ alkyl and aryl, which alkyl and aryl are optionally substituted with 1 substituent independently selected from halo, alkyl or CN, O—$C_{1-6}$ alkyl, and $CF_3$.

Even more preferably, $R_2$, $R_2$', and $R_2$" are each independently selected from the group consisting of $C_{1-6}$ alkyl which alkyl are optionally substituted with 1 substituent independently selected from the group of aryl, $CF_3$, CN, $OR^{20}$, $N(R^{20})_2$, and each optional aryl substituent is optionally substituted with halo, $NO_2$, alkyl, $CF_3$; wherein $R_{20}$ is a member selected from the group consisting of H, $C_{1-6}$ alkyl; and $R_{22}$ is a member selected from the group consisting of $C_{1-6}$.

In a further preferred embodiment, $R_2$, $R_2$', and $R_2$" are each independently selected from —$R_3$Ph, —$R_3$—O—$R_3$, —$R_3$—O—$R_3$—Ph, —$R_3$—$NH_2$ pyridine, and cyclic aliphatic hydrocarbons, wherein $R_3$ is a straight or branched alkyl having from 1 to 8 carbon atoms.

In still a further preferred embodiment, $R_2$, $R_2$', and $R_2$" are each independently selected from propyl, isopropyl, cyclopentyl, 3-pyridyl, methyl, butyl, 1-amino-3-methylpropyl, —$CH_2OCH_2CH_3$, —$CH_2OCH_2Ph$, —$CH_2Ph$-4—$NO_2$, and —$CH_2NH_2$.

It is most preferred that $R_2$ is isopropyl and $R_2$' and $R_2$" are methyl or that $R_2$ is methyl and $R_2$' and $R_2$" are isopropyl.

Compositions of this invention may also have the formula:

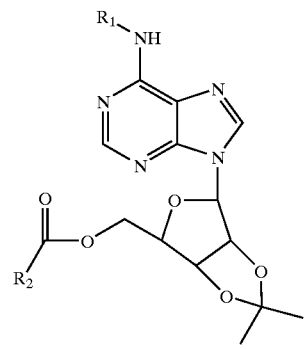

wherein $R_2$ is selected from the possible $R_2$ substituents identified above and wherein $R_2$ is preferably —$R_3$Ph, —$R_3$—O—$R_3$, —$R_3$—O—$R_3$—Ph, —$R_3$—$NH_2$, pyridine, and cyclic aliphatic hydrocarbon wherein $R_3$ is a straight or branched alkyl having from 1 to 8 carbon atoms and wherein $R_2$ is most preferably selected from propyl, isopropyl, cyclopentyl, 3-pyridyl, methyl, butyl, 1-amino-3-methylpropyl, —$CH_2OCH_2CH_3$, —$CH_2OCH_2Ph$, —$CH_2Ph$-4—$NO_2$, and —$CH_2NH_2$.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyolopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'''R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group -R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in Schemes 1–5. Compound I can be prepared through reaction of the corresponding primary amino compound, $R_1NH_2$, through heating with commercially available 6-chloroadenosine in the appropriate solvent (e.g. n-butanol, dimethylformamide, and ethanol). The primary amino compound, $R_1NH_2$, is either commercially available or can be prepared as previously described (International Patent Application WO 98/08855). The pro-drug esters of this invention can be prepared using all of the known methods for ester formation which are included by reference (see Jerry March Organic synthesis and Richard Larock— Methods of Organic Synthesis), and more preferably by those outlined in this application.

Scheme 1

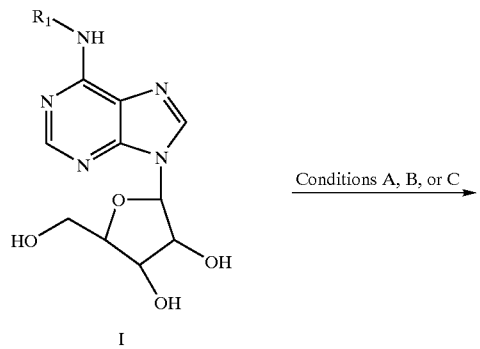

I

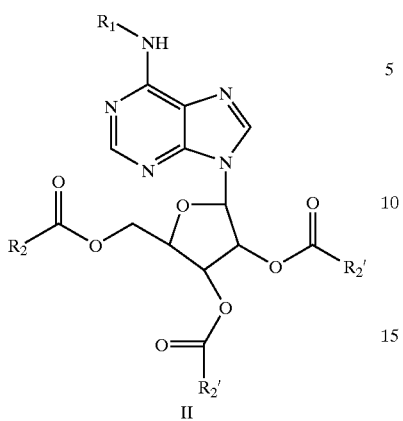

II

The following methods of ester pro-drug formation were used to make the compounds of this invention Scheme 1: Conditions A—corresponding anhydride, and pyridine; Conditions B—corresponding carboxylic acid, dicyclohexylcarbodiimide (DCC), dimethylaminopyridine (DMAP), pyridine, dimethylformamide (DMF); Conditions C—corresponding acid chloride, DMF, and pyridine.

The differential protection of the 2', 3', and 5' hydroxyl groups provides a method for preparing different pro-drug esters at each position, or like ester groups at two positions and dissimilar ester pro-drugs at a third position. This differentiation may prove advantageous, since the rate of cleavage of the respective ester pro-drugs are known to vary based on how readily they are cleaved by plasma esterases or first pass metabolic enzymes. The in vivo cleavage of the respective triple pro-drugs will provide mono and diesters which may have different in vivo properties such as favorable partitioning, and half-life properties. Scheme 2 outlines one method to prepare similar pro-drug esters at the 2' and 3' hydroxyl groups, but a different ester pro-drug at the 5' position. This is accomplished through the formation of an acetonide [Evans, Parrish and Long Carbohydrat. Res., 3, 453 (1967)] at the 2' and 3' positions followed by ester formation at the 5' hydroxyl position. Brief treatment of compound IV with anhydrous hydrochloric acid in dioxane affords the free 2' and 3' hydroxyl groups; however, the ester on the 5' hydroxyl group remains intact. Then, compound V is esterified under conditions A, B, or C to afford identical ester pro-drugs at the 2' and 3' positions.

Scheme 2

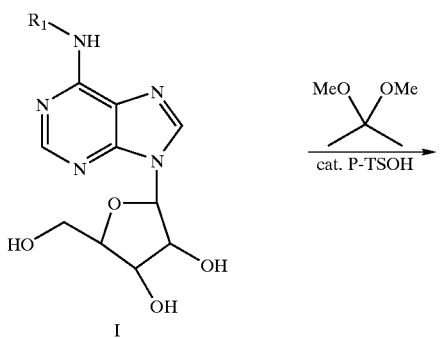

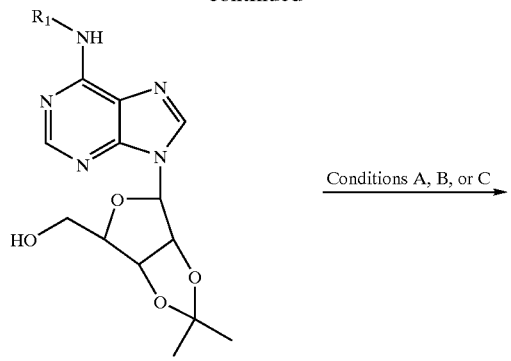

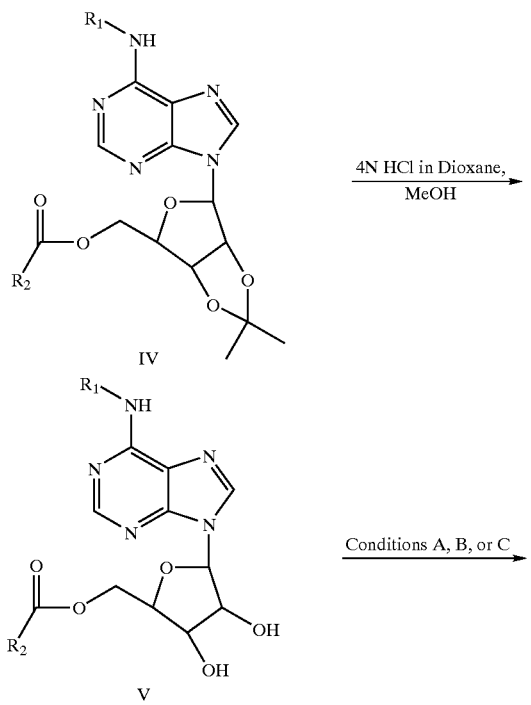

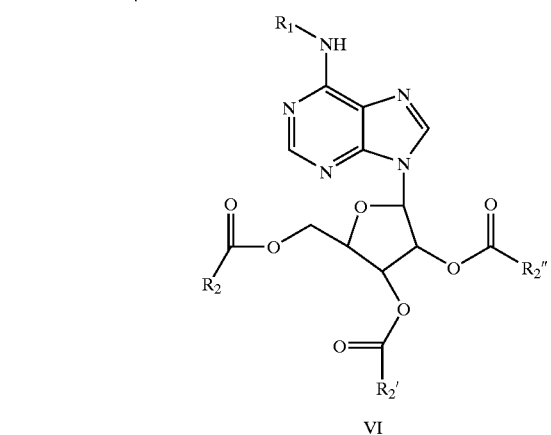

VI

The 5' and 3' hydroxyl groups can be protected by formation of a tetra-t-butoxydisiloxane-1,3-diylidene derivative as illustrated in Scheme 3. The formation of VII can be achieved through the reaction of the commercially available disilylchloride reagent with compound I using pyridine as the solvent [Markiewicz, Nowakowska, and Adrych—Tetrahedron Lett., 29, 1561 (1988)]. Then, the ester bond of compound VII can be formed using conditions A, B, or C followed by deprotection of the 3' and 5' hydroxyl groups using tetrabutylammonium fluoride [TBAF—Markiewicz, Nowakowska, and Adrych—Tetrahedron Lett., 29, 1561 (1988)] to afford compound IX. The di(p-methoxyphenyl)methyl ether [DMT group, Khorana Pure Appl. Chem 17, 349 (1968)] can be used to protect the 5' hydroxyl group selectively followed by esterification of the 3' hydroxyl group using conditions A, B, or C. The DMT group of compound XI can be removed using 3% trichloroacetic acid in methylene chloride or nitromethane/methanol [Takaku, Morita, Sumiuchi Chem. Lett. 1661 (1983)] followed by esterification of the 5' hydroxyl group using conditions A, B, or C.

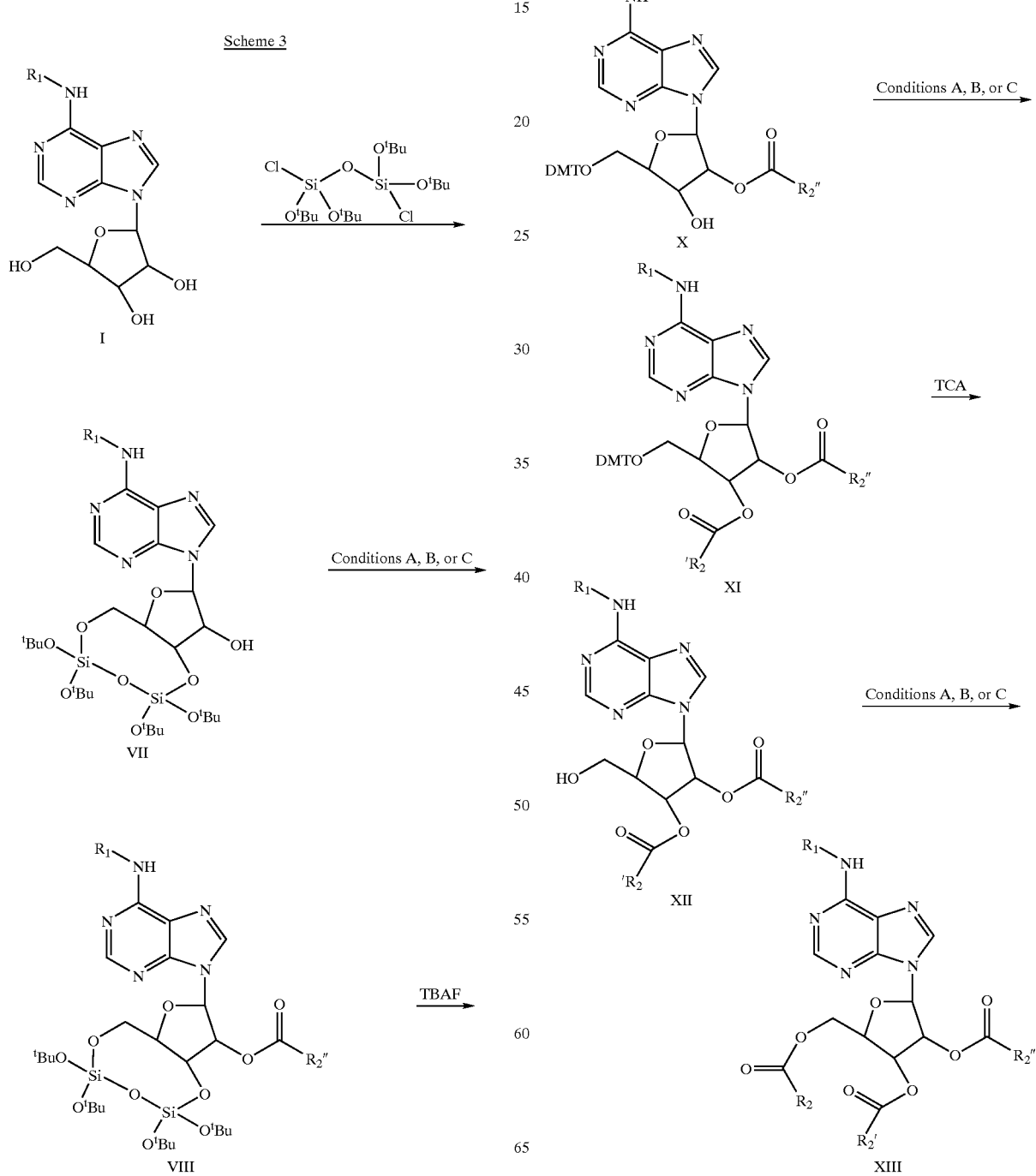

Scheme 3

Compound 1 has been shown to be a potent, selective adenosine $A_1$ agonist [Snowdy, Pfister, Lum, Nelson, Schow, Wang, Belardinelli Abst 114 at The 6$^{th}$ International Symposium on Adenosine and Adenine Nucleotides and International Patent Application WO 98/08855], and the preparation has been described previously (International Patent Application WO 98/08855). Compound 1 was reacted with acetic anhydride in pyridine (Conditions A) to afford the triacetoxy derivative 2 as a triple pro-drug of compound 1 (Scheme 4). The tri-propionate derivative 3 was prepared using the B conditions of dicyclohexylcarbodiimide, dimethylaminopyridine, pyridine, and dimethylformamide as illustrated in Scheme 5.

Scheme 4

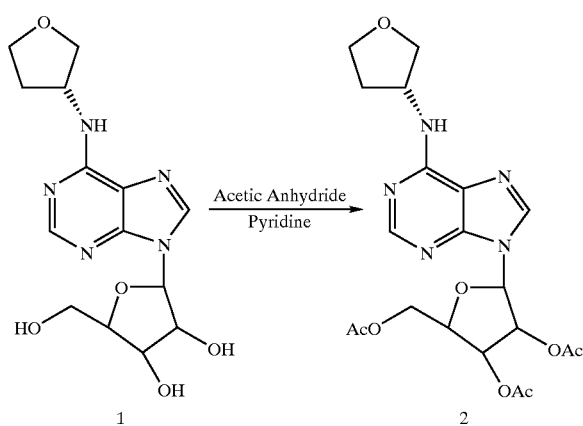

Scheme 5

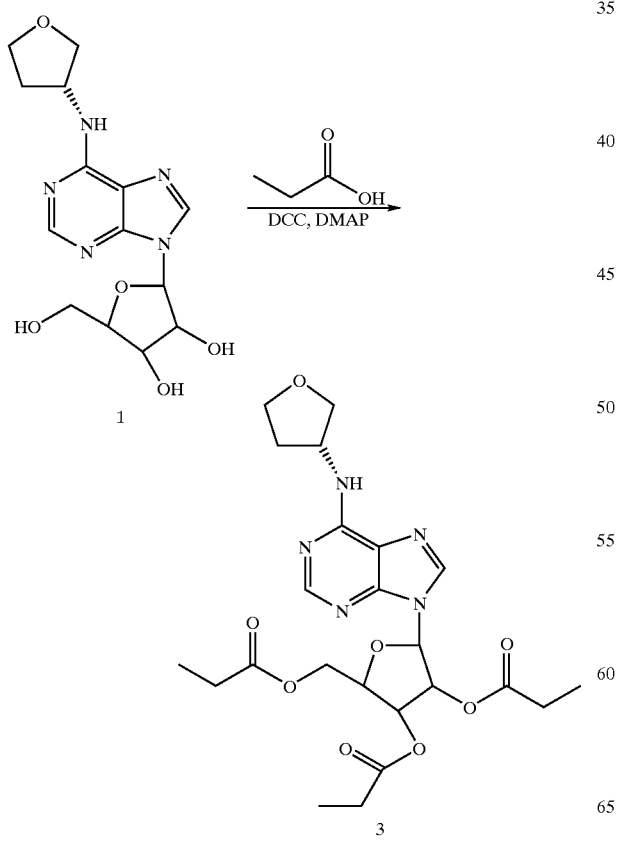

Scheme 6

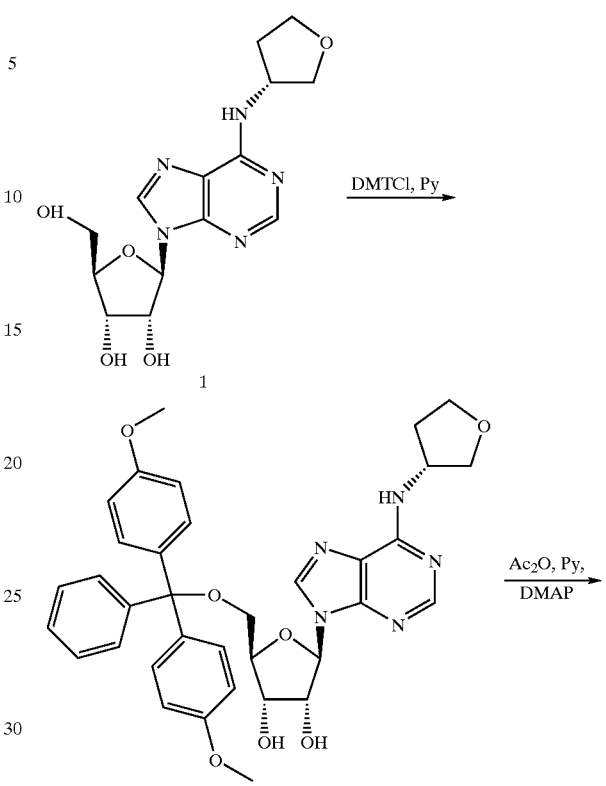

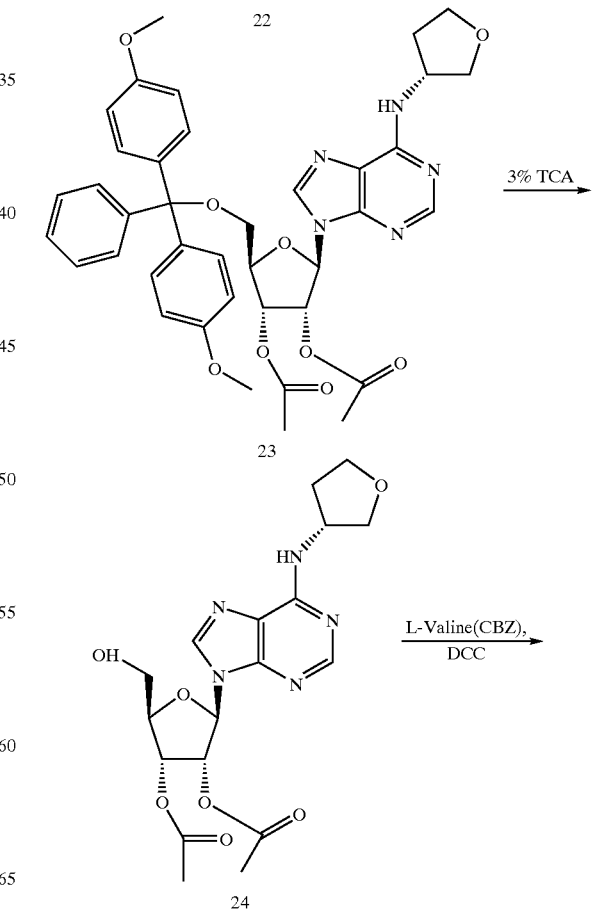

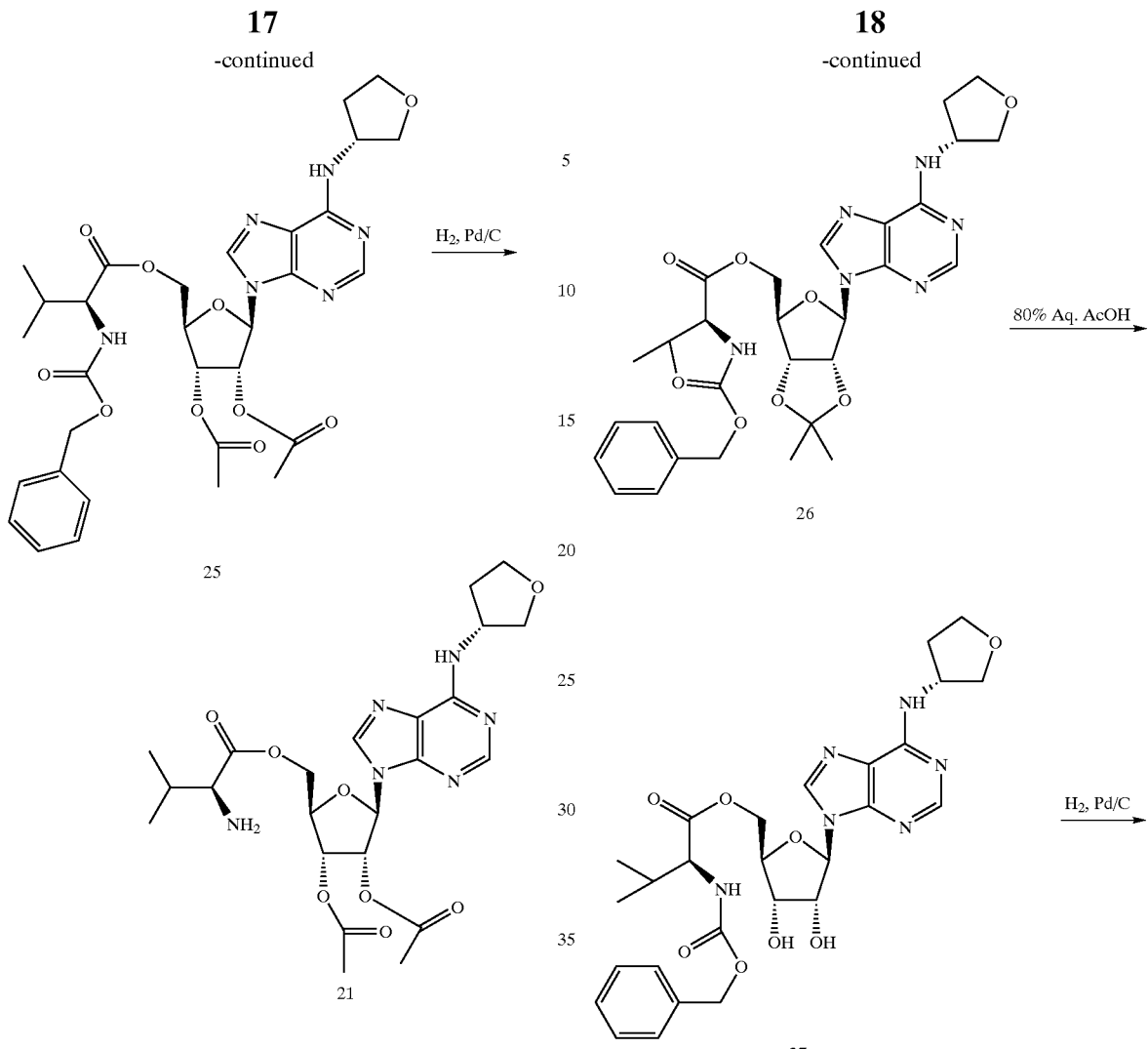

Compound 21 was prepared using the DMT protecting group as described above for selective 5' protection followed by introduction of the diacetoxy groups to afford 23 (Scheme 6). After removal of the 5' DMT group, an ester was made at the 5' position using N-CBZ valine. Hydrogenolysis of the CBZ group afforded compound 21. Compound 20 was prepared from the isopropylidene derivative 15A as illustrated in Scheme 7.

Scheme 7

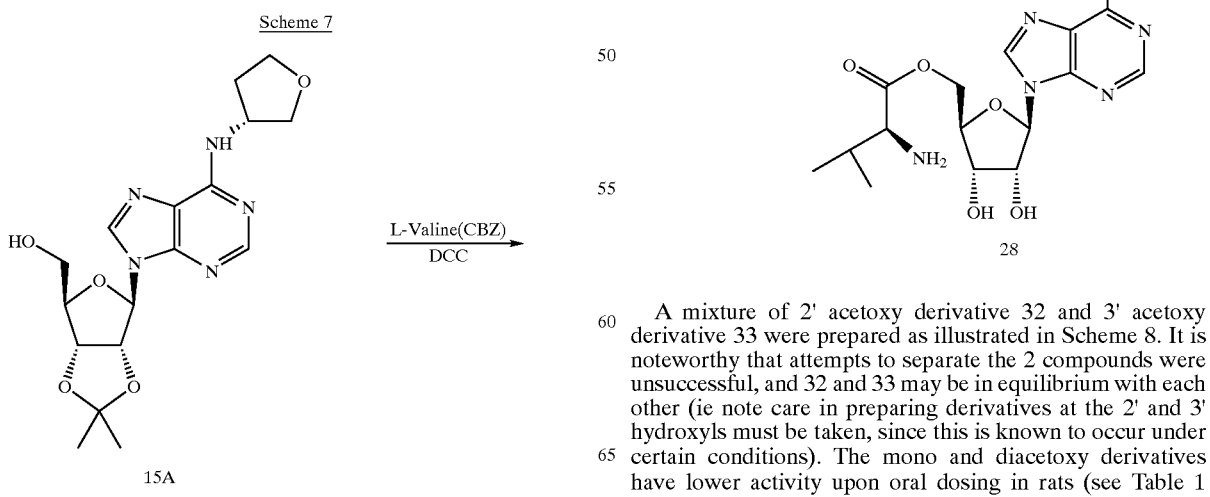

A mixture of 2' acetoxy derivative 32 and 3' acetoxy derivative 33 were prepared as illustrated in Scheme 8. It is noteworthy that attempts to separate the 2 compounds were unsuccessful, and 32 and 33 may be in equilibrium with each other (ie note care in preparing derivatives at the 2' and 3' hydroxyls must be taken, since this is known to occur under certain conditions). The mono and diacetoxy derivatives have lower activity upon oral dosing in rats (see Table 1 compounds 31 and 32/33).

Scheme 8

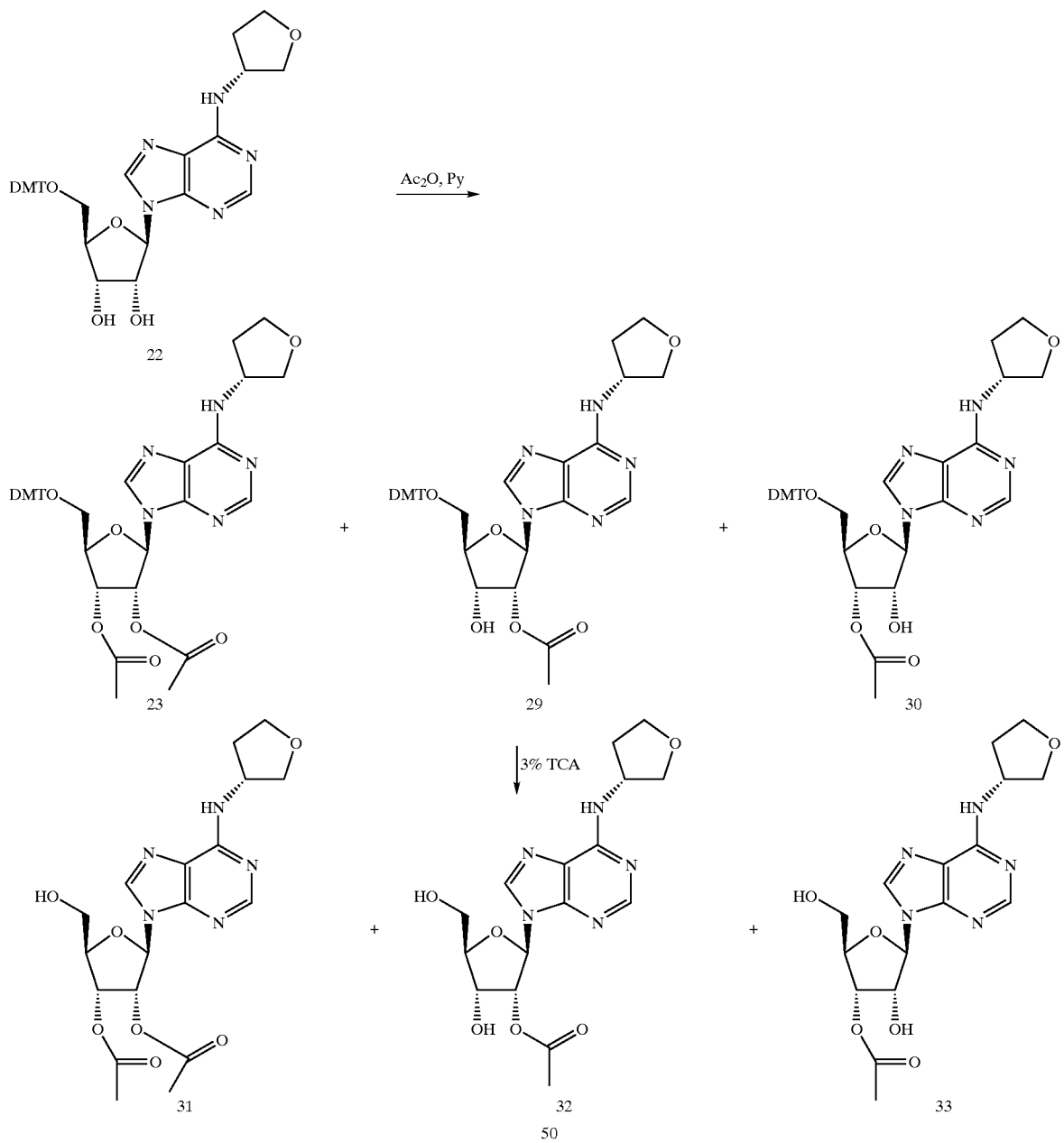

The pro-drug compositions of this invention are concentrated in vivo as $A_1$ receptor agonists for the treatment of coronary electrical disorders such as supraventricular tachycardias, including atrial fibrillation, atrial flutter, and AV nodal re-entrant tachycardia. The compositions may be administered orally, intravenously, through the epidermis or by any other means known in the art for administering a therapeutic agents.

The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. These dosage units may be administered one to ten times daily for acute or chronic disorders. No unacceptable toxicological effects are expected when compounds of the invention are administered in accordance with the present invention.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methane sulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

This example is a method for synthesizing pro-drugs of this invention using condition A—corresponding anhydride and pyridine as the solvent.

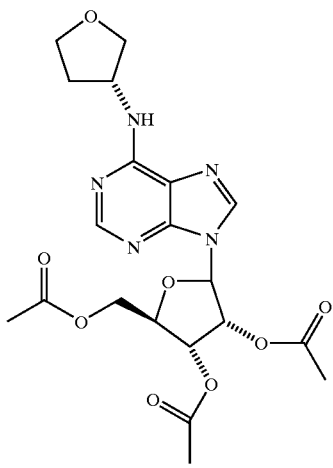

(5-{6-[((3R)oxolan-3-yl)amino]purin-9-yl}(2R, 3R, 4R)-3, 4-diacetyloxyoxolan-2-yl)methyl acetate (2).

To a solution of compound 1 (1.68 g, 5 mmol) and dimethylaminopyridine (100 mg, 0.82 mmol) in pyridine (10 mL) at 23 C. was added acetic anhydride (1 mL, 10.6 mmol). After 3 h at 23 C., the reaction was concentrated in vacuo. The residue was dissolved in methylene chloride (100 mL), washed with water (3×20 mL), and dried (Na$_2$SO$_4$). After concentration in vacuo, the residue was purified by flash chromatography (methylene chloride: methanol 20:1 followed by 9:1) to afford compound 2: $^1$H NMR(CDCl$_3$) δ1.93 (s, 3H), 1.97 (s, 3H), 2.03 (s, 3H), 2.20–2.33 (m,1H), 3.70–3.80(m,2H), 3.83–3.95(m,2H), 4.25–4.40 (m, 3H), 4.78–4.87 (m, 1H), 5.58 (dd, 1H), 5.85 (dd, 1H), 6.13 (d, 1H), 6.50 (br s, 1H), 7.93 (s,1H), 8.27(s,1H).

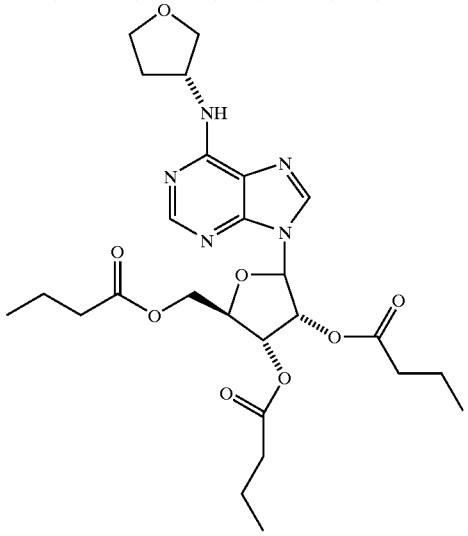

(5-{6-[((3R)oxolan-3-yl)amino]purin-9-yl}(2R, 3R, 4R)-3, 4-dibutanoyloxyoxolan-2-yl)methyl butanoate (4).

Compound 4 was prepared in the manner of compound 2 substituting butyric anhydride for acetic anhydride to afford compound 4 after flash column chromatography: $^1$H NMR (CDCl$_3$) δ0.84–1.03 (m, 9H), 1.53–1.74 (m, 6H), 2.02–2.13 (m,1H), 2.24–2.41(m,7H), 3.79–3.93(m,2H), 4.03–4.12(m, 2H), 4.34–4.47 (m, 3H), 5.57–5.67 (m, 1H), 5.84–5.89 (m, 1H), 6.15 (m, 1H), 7.93–8.02 (s,1H), 8.35–8.45 (s,1H).

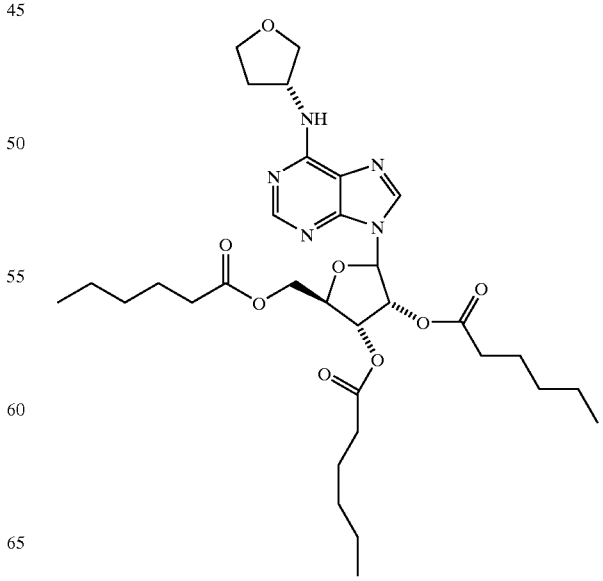

(5-{6-[((3R)oxolan-3-yl)amino]purin-9-yl}(2R, 3R, 4R)-3,4-dihexanoyloxyoxolan-2-yl)methyl hexanoate (5).

Compound 5 was prepared in the manner of compound 2 substituting hexanoic anhydride for acetic anhydride to afford compound 4 after flash column chromatography: Compound 4 was prepared in the manner of compound 2 substituting butyric anhydride for acetic anhydride to afford compound 4 after flash column chromatography: $^1$H NMR (CDCl$_3$) δ0.85–0.93 (m, 9H),1.11–1.73(m,18H), 2.03–2.14 (m,1H), 2.21–2.48(m,7H), 3.79–3.93(m,2H), 4.03–4.09(m, 2H), 4.34–4.43 (m, 3H), 4.75–4.83 (m, 1H), 5.54 (dd, 1H), 5.84 (dd, 1H), 6.19 (m, 1H), 7.85–8.02 (br s,1H), 8.39 (br s,1H).

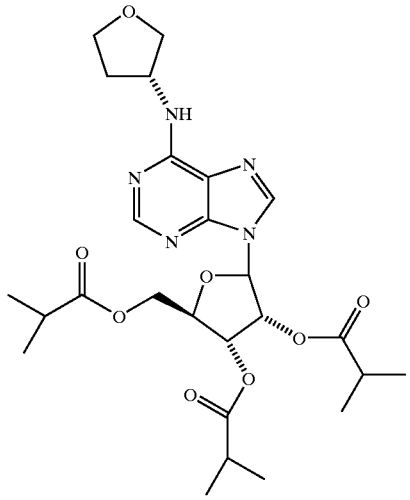

(5-{6-[((3R)oxolan-3-yl)amino]purin-9-yl}(2R, 3R, 4R)-3,4-bis(2-methylpropanoyloxy)oxolan-2-yl)methyl 2-methylpropanoate (6).

Compound 6 was prepared in the manner of compound 2 substituting isobutyric anhydride for acetic anhydride to afford compound 6 after flash column chromatography: $^1$H NMR(CDCl$_3$) δ0.95–1.22 (m, 18H), 1.93–2.05 (m, 1H), 2.32–2.43 (m,1H), 2.52–2.64(m,2H), 3.85–3.92(m,2H), 3.94–4.05(m,2H), 4.31–4.43 (m, 3H), 4.83–4.92(m, 1H), 5.64 (dd, 1H), 5.83 (dd, 1H), 6.15 (d, 1H), 6.30 (br s, 1H), 7.92 (s,1H), 8.38(s,1H).

EXAMPLE 2

This example is a method for synthesizing pro-drugs of this invention using conditions B—the corresponding carboxylic acid, dicyclohexylcarbodiimide (DCC), dimethylaminopyridine (DMAP), and a solvent of DMF and/or pyridine.

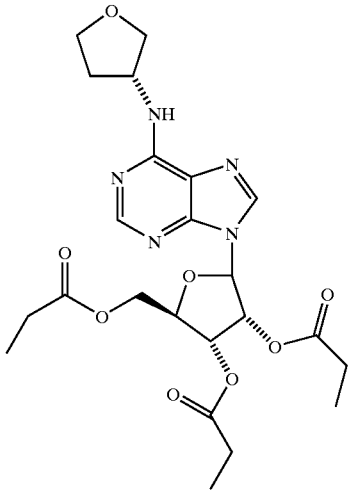

(2-{6-[((3R)oxolan-3-yl)amino]purin-9-yl}(3R, 4R, 5R)-4-propanoyloxy-5-(propanoyloxymethyl)oxolan-3-yl propanoate (7).

To a solution of compound 1 (500 mg, 1.4 mmol) and propionic acid (296 mg, 4.0 mmol) was added dicyclohexylcarbodiimide (1400 mg, 6.8 mmol), dimethylaminopyridine (170 mg, 1.4 mmol) in pyridine (10 mL) at 23 C. After 16 h at 23 C., the reaction was filtered through a sintered glass funnel and concentrated in vacuo. After azeotroping with toluene in vacuo, the residue was dissolved in ethyl acetate (150 mL), washed with citric acid (10% aq. 50 mL), washed with bicabonate (1N, 2×100 mL), and dried (Na$_2$SO$_4$). After concentration in vacuo, the residue was purified by application of flash chromatography (ethyl acetate: hexane 1:1 then 2:1) to afford compound 7: $^1$H NMR(CDCl$_3$) δ0.95–1.11 (m, 9H), 1.83–1.93 (m,1H), 2.19–2.38(m,6H), 3.70–3.82(m,2H), 3.83–3.95(m,2H), 4.24–4.45 (m, 3H), 5.57 (dd, 1H), 5.85 (dd, 1H), 6.09 (d, 1H), 6.45 (br s, 1H), 7.92 (s,1H), 8.25(s,1H).

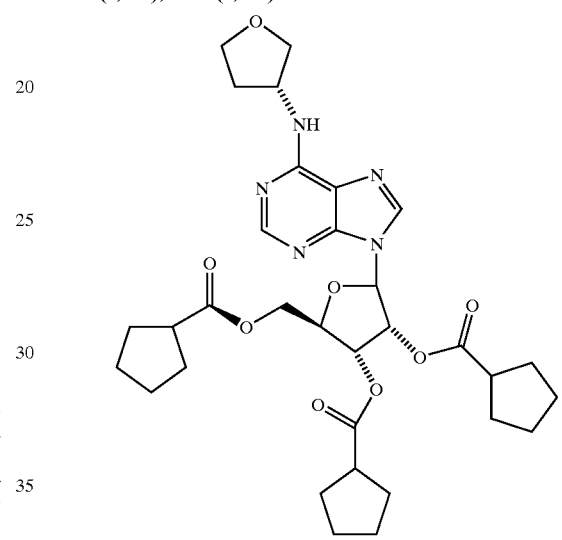

2-{6-[((3R)oxolan-3-yl)amino]purin-9-yl}(3R, 4R, 5R)-4-cyclopentylcarbonyloxy-5-(cyclopentylcarbonyloxymethyl) oxolan-3-yl cyclopentanecarboxylate (8).

Compound 8 was prepared in the manner of compound 7 substituting cyclopentanecarboxylic acid for propionic acid to afford compound 8 after flash colunm chromatography: $^1$H NMR(CDCl$_3$) δ1.4–2.1 (m, 25H), 2.2–2.35 (m,1H), 2.61–2.75(m,4H), 3.72–3.82(m,2H), 3.83–3.95(m,2H), 4.25–4.40 (m, 3H), 5.56 (dd, 1H), 5.80 (dd, 1H), 6.13 (d, 1H), 6.45 (br s, 1H), 7.92 (s,1H), 8.29(s,1H).

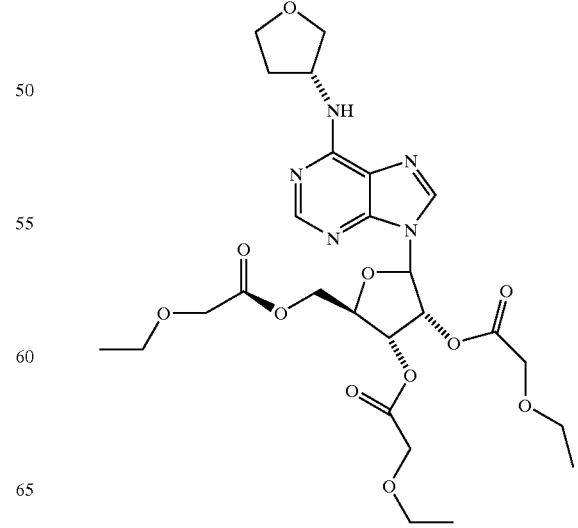

2-{6-[((3R)oxolan-3-yl)amino]purin-9-yl}(3R, 4R, 5R)-4-(2-ethoxyacetyloxy)-5-[(2-ethoxyacetyloxy)methyl]oxolan-3-yl 2-ethoxyacetate (9).

Compound 9 was prepared in the manner of compound 7 substituting ethoxyacetic acid for propionic acid to afford compound 9 after flash column chromatography: $^1$H NMR (CDCl$_3$) δ1.15–1.28 (m, 9H), 1.89–1.97 (m, 1H), 2.28–2.41 (m, 1H), 3.43–3.61 (m, 6H),3.75-3.85(m,2H), 3.93–4.00 (m,2H), 4.01–4.15 (m, 6H), 4.38–4.51 (m, 3H), 4.81–4.87 (m, 1H), 5.71–5.75 (m, 1H), 6.03–6.07 (m, 1H), 6.18–6.19 (m, 1H), 6.23–6.29 (m, 1H), 8.05 (br s,1H), 8.34(br s,1H).

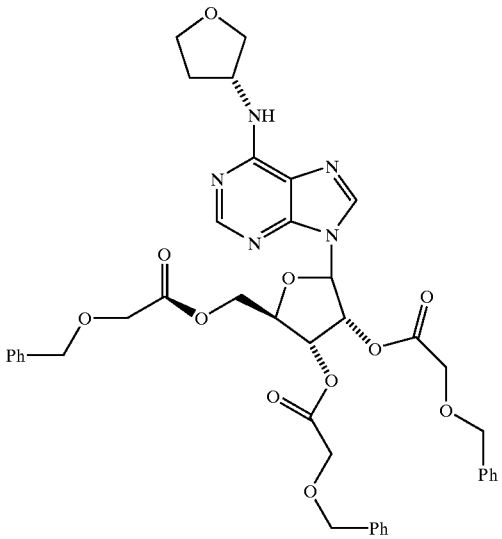

(5-{6-[((3R)oxolan-3-yl)amino]purin-9-yl}(2R, 3R, 4R)-3,4-bis[2-(phenylmethoxy)acetyloxy]oxolan-2-yl)methyl 2-(phenylmethoxy)acetate (10).

Compound 10 was prepared in the manner of compound 7 substituting benzyloxyacetic acid for propionic acid to afford compound 10 after flash column chromatography: $^1$H NMR(CDCl$_3$) δ1.92–2.01 (m, 1H1), 2.32–2.45 (m, 1H), 2.20–2.33 (m,1H), 3.75–3.91 (m,2H), 3.95–4.21 (m,8H), 4.41–4.67 (m, 9H), 4.83–4.93 (m, 1H), 5.81–5.86 (m, 1H), 6.07–6.18 (m, 2,), 6.23–6.29 (m, 1H), 7.14–7.41 (m, 15H), 7.99 (s,1H), 8.35(s,1H).

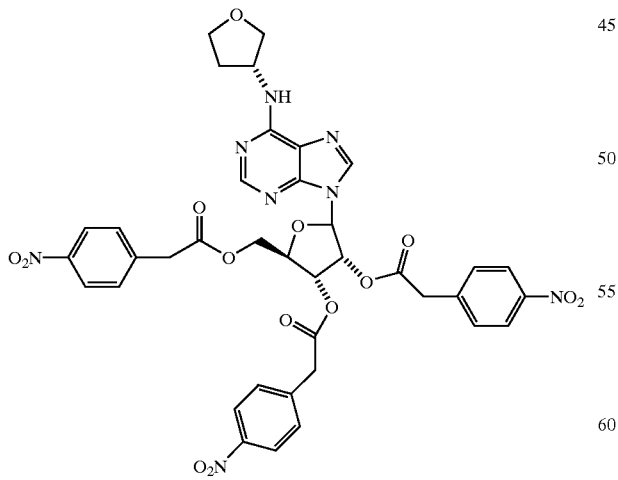

2-{6-[((3R)oxolan-3-yl)amino]purin-9-yl}(3R, 4R, 5R)-4-(2-nitrophenyl)acetyloxy]-5-{[(2-(4-nitrophenyl)acetyloxy]methyl}oxolan-3-yl 2-(4-nitrophenyl)acetate (11).

Compound 11 was prepared in the manner of compound 7 substituting (4-nitrophenyl)acetic acid for propionic acid to afford compound 11 after flash column chromatography: $^1$H NMR(CDCl$_3$) δ1.91–1.99 (m,1H), 2.32–2.43 (m, 1H), 3.52–4.03 (m,10H), 4.78–4.84 (m, 1H), 3.83–3.95(m,2H), 5.67 (dd, 1H), 5.87 (dd, 1H), 6.10 (d, 1H), 6.13 (br s, 1H), 7.23–7.41 (m, 6H), 7.61 (s,1H), 8.05–8.17 (m, 6H), 8.28(s, 1H).

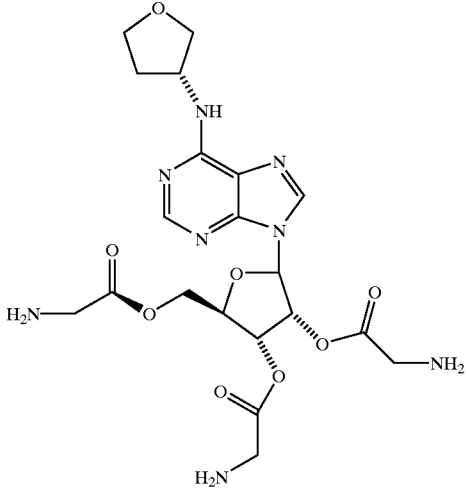

2-{6[((3R)oxolan-3-yl)amino]purin-9-yl}(3R, 4R, 5R)-4-(2-aminoacetyloxy)-5-[(2-aminoacetyloxy)methyl]oxolan-3-yl 2-aminoacetate (12).

Compound 12 was prepared in the manner of compound 7 substituting N-BOC glycine for propionic acid to afford compound 12 after deprotection by brief exposure to 4 N HCl in dioxane (5 min) followed by concentration in vacuo to afford the HCl salt of 12 (note: flash chromatography was performed at the tris N-BOC glycine stage as described for compound 7): $^1$H NMR(CD$_3$OD) δ1.85–1.94 (m, 1H), 2.23–2.38 (m, 1H), 2.20–2.33 (m,1H), 3.75–3.98 (m,10H), 4.28–4.49 (m,4H), 4.73–4.84 (m, 1H), 5.7–6.08 (m, 9H), 7.90 (br s,1H), 8.25(br s,1H).

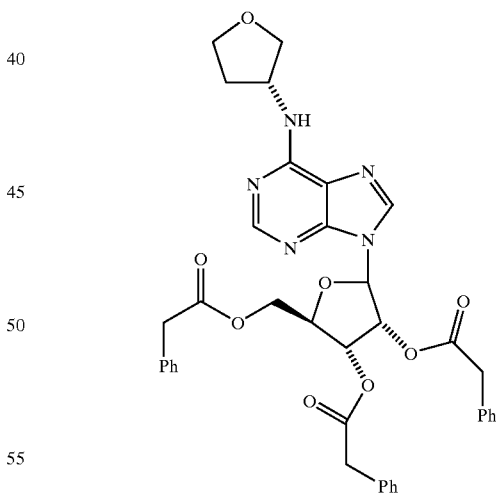

(5-{6-[((3R)oxolan-3-yl) amino]purin-9-yl}(2R, 3R, 4R)-3,4-bis(2-phenylethanoyloxy)oxolan-2-yl)methyl 2-phenylethananoate (13).

Compound 13 was prepared in the manner of compound 7 substituting 2-phenylethanoic acid for propionic acid to afford compound 13 after flash column chromatography: $^1$H NMR(CDCl$_3$) δ1.93–2.03 (m, 1H), 2.32–2.43 (m, 1H), 3.38 (s, 2H), 3.43 (s, 2H), 3.63 (s, 3H), 3.75–4.04 (m,2H), 4.23–4.41 (m,3H), 4.82–4.89 (m, 1H), 5.57–5.68 (m, 2H), 6.09 (d, 1H), 6.42 (br s, 1H), 7.08–7.35 (m, 15H), 7.52 (s,1H), 8.36(s,1H).

EXAMPLE 3

This example is a method for synthesizing pro-drugs of this invention using conditions C—the corresponding acid chloride in pyridine.

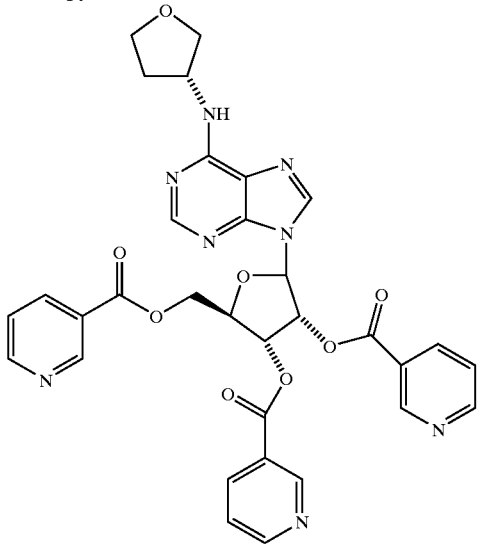

(5-{6-[((3R)oxolan-3-yl)amino]purin-9-yl}(2R, 3R, 4R)-3,4-di(3-pyridylcarbonyloxy)oxolan-2-yl)methyl pyridine-3-carboxylate (14).

To a solution of compound 1 (200 mg, 0.59 mmol) in pyridine (10 mL) was added nicotinoyl chloride hydrochloride at 23 C. After 24 h at 23 C., the reaction was filtered through a sintered glass funnel followed by concentration in vacuo. After azeotroping with toluene in vacuo, the residue was applied directly to flash chromatography (methylene chloride: methanol 20:1 followed by 9:1) to afford compound 14: $^1$H NMR(CDCl$_3$) δ1.91–1.97 (m, 1H), 2.31–2.42 (m,1H), 3.75–3.88(m,2H), 3.92–4.05 (m,2H), 4.70–4.93 (m, 3H), 4.78–4.87 (m, 1H), 6.13 (d, 1H), 6.32–6.38 (m, 2H), 6.55 (dd, 1H), 7.31–7.42 (m, 3H),7.91 (s,1H), 8.15–8.34 (m,4H), 8.73–8.79 (m, 3H), 9.10 (s, 1H), 9.13 (s, 1H), 9.27 (s, 1H).

EXAMPLE 4

This example is a method for synthesizing pro-drugs of this invention as illustrated in Scheme 2, wherein the 2' and 3' hydroxyl groups are protected as similar ester groups, but the 5' hydroxyl group has a different ester group.

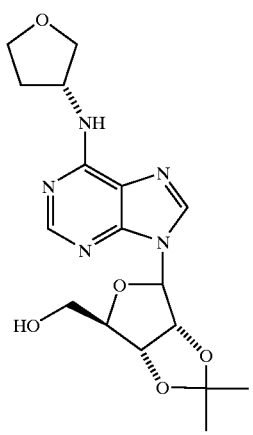

Intermediate—(4-{6-[((3R)oxolan-3-yl)amino]purin-9-yl}(1R, 2R, 5R)-7,7-dimethyl-3,6,8-trioxabicyclo[3.3.0]oct-2-yl)methan-1-ol (15A)

To a solution of compound 1 (2.0 g, 6.0 mmol) and 2,2-dimethoxypropane (1.2 g, 11.8 mmol) in dimethylformamide (20 mL) was added p-toluenesulfonic acid (50 mg, 0.26 mmol) at 70° C. After 48 h at 70 C., the reaction was concentrated in vacuo to afford a solid. The solid was dissolved in methanol (3 mL), then triturated with ethyl ether (50 mL). The resultant crystals were collected by vacuum filtration to afford the intermediate 15A.

Intermediate—(4-{6-[((3R)oxolan-3-yl)amino]purin-9-yl}(1R, 2R, 5R)-7,7-dimethyl-3,6,8-trioxabicyclo[3.3.0]oct-2-yl)methyl acetate (15B)

The 5' acetoxy group was introduced in the manner of Example 1, compound 2 to afford the intermediate 15B.

Intermediate—(5-{6-[((3R)oxolan-3-yl)amino]purin-9-yl}(3S, 2R, 4R)-3,4-dihydroxyoxolan-2-yl)methyl acetate (15C)

To a solution of intermediate 15B (200 mg) and methanol (2 mL) was added anhydrous 4N HCl in dioxane (1 mL) at 23 C. in a sealed tube. After 5 min at 23 C., the reaction was concentrated in vacuo (note: sodium hydroxide trap was used to trap HCl). After azeotroping with chloroform in vacuo, the intermediate 15C was obtained as the hydrochloride salt.

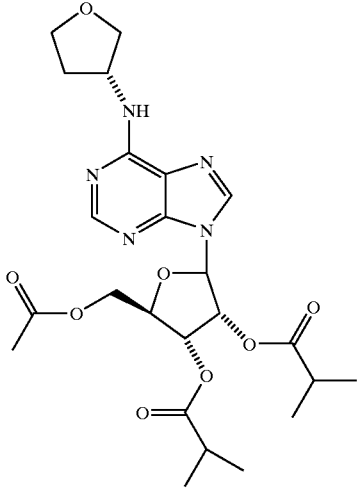

2-{6-[((3R)oxolan-3-yl)amino]purin-9-yl}(3R, 4R, 5R)-5-(acetyloxymethyl)-4-(2-methylpropanoyloxy)oxolan-3-yl 2-methylpropanoate (15).

Compound 15 was prepared from 15C in the manner of compound 2 substituting isobutyric anhydride for acetic anhydride: $^1$H NMR(CDCl$_3$) δ1.05–1.22 (m, 12H), 1.93–2.05 (m, 1H), 2.08 (s, 3H), 2.29–2.39 (m,1H), 2.52–2.63(m,2H), 3.75–3.87(m,2H), 3.94-4.05(m,2H), 4.31–4.43 (m, 3H), 4.82–4.85(m, 1H), 5.64 (dd, 1H), 5.83 (dd, 1H), 6.14 (d, 1H), 6.43 (br s, 1H), 7.89 (s,1H), 8.35(s, 1H).

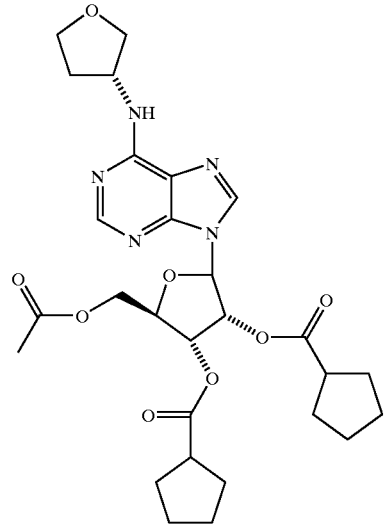

(5'-{6-[((3R)oxolan-3-yl)amino]purin-9-yl}(2R, 3R, 4R)-3,4-dicyclopentylcarbonyloxyoxolan-2-yl)methyl acetate (16).

Compound 16 was prepared in the manner of compound 15 utilizing cyclopentanecarboxylic acid under conditions B for introduction of the ester groups at the 2' and 3' hydroxyl groups, and acetic anhydride under conditions A for the introduction of the 5' hydroxyl group: $^1$H NMR(CDCl$_3$) δ1.45–1.97 (m, 16H), 2.07 (s, 3H), 2.28–2.39 (m,1H), 2.64–2.76(m,2H), 3.75-3.86(m,2H), 3.94–4.03(m,2H), 4.32–4.43 (m, 3H), 4.82–4.91 (m, 1H), 5.64 (dd, 1H), 5.83 (dd, 1H), 6.13 (d, 1H), 6.43 (br s, 1H), 7.88 (s,1H), 8.32(s, 1H).

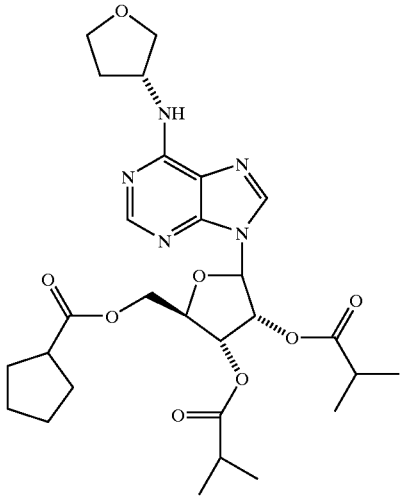

2-{6-[((3R)oxolan-3-yl)amino]purin-9-yl}(3R, 4R, 5R)-5-(cyclopentylcarbonyloxymethyl)-4-(2-methylpropanoyloxy)oxolan-3-yl 2-methylpropanoate (17).

Compound 17 was prepared in the manner of compound 15 utilizing cyclopentanecarboxylic acid under conditions B for introduction of the ester group at the 5' hydroxyl group, and isobutyric anhydride under conditions A for the introduction of the 2' and 3' hydroxyl groups: $^1$H NMR(CDCl$_3$) δ1.05–1.23 (m, 12H), 1.52–2.05 (m, 8H), 2.26–2.38 (m,1H), 2.49–2.63(m,2H), 2.71–2.79 (m, 1H), 3.75–3.87(m,2H), 3.94–4.06(m,2H), 4.34–4.45 (m, 3H), 4.78–4.86(m, 1H), 5.58 (dd, 1H), 5.81 (dd, 1H), 6.17 (d, 1H), 6.95 (br s, 1H), 7.97 (s,1H), 8.37(s,1H).

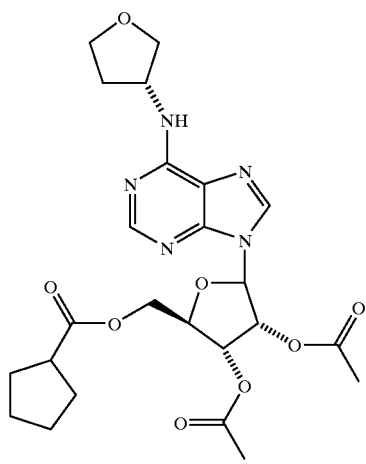

2-{6-[((3R)oxolan-3-yl)amino]purin-9-yl}(3R, 4R, 5R)-4-acetyloxy-5-(cyclopentylcarbonyloxymethyl)oxolan-3-yl acetate (18).

Compound 18 was prepared in the manner of compound 15 utilizing cyclopentanecarboxylic acid under conditions B for introduction of the ester group at the 5' hydroxyl group, and acetic anhydride under conditions A for the introduction of the 2' and 3' hydroxyl groups: $^1$H NMR(CDCl$_3$) δ1.52–2.02 (m, 8H), 2.03 (s, 3H), 2.13 (s, 3H), 2.31–2.42 (m,1H), 2.71–2.82(m,1H), 3.75–3.90(m,2H), 3.95–4.05(m, 2H), 4.37–4.46 (m, 3H), 4.83-4.91(m, 1H), 5.59 (dd, 1H), 5.84 (dd, 1H), 6.18 (d, 1H), 6.24–6.35 (br s, 1H), 7.93 (s,1H), 8.38(s,1H).

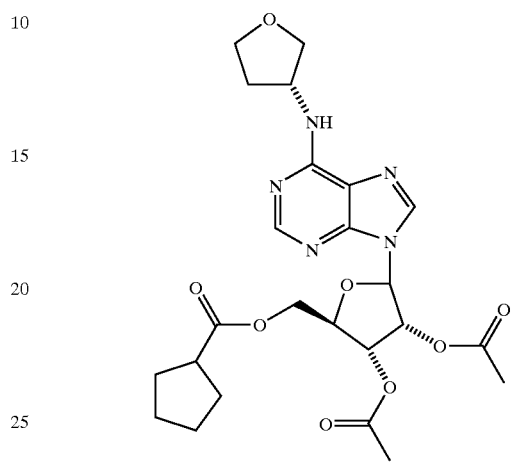

(5-{6-[((3R)oxolan-3-yl) amino]purin-9-yl}(2R, 3R, 4R)-3,4-diacetyloxyoxolan-2-yl)methyl 2-methylpropanoate (19).

Compound 19 was prepared in the manner of compound 15 utilizing isobutyric anhydride under conditions A for introduction of the ester group at the 5' hydroxyl group, and acetic anhydride under conditions A for the introduction of the 2' and 3' hydroxyl groups: $^1$H NMR(CDCl$_3$) δ1.15–1.22 (m, 6H), 2.02 (s, 3H),2.12 (s, 3H), 2.30–2.42 (m, 1H), 2.55-2.68(m,1H), 3.75–3.87(m,2H), 3.95–4.01(m,2H), 4.34–4.44 (m, 3H), 5.63 (dd, 1H), 5.87 (dd, 1H), 6.07 (br d, 1H), 6.17 (d, 1H), 7.92 (s,1H), 8.34(s,1H).

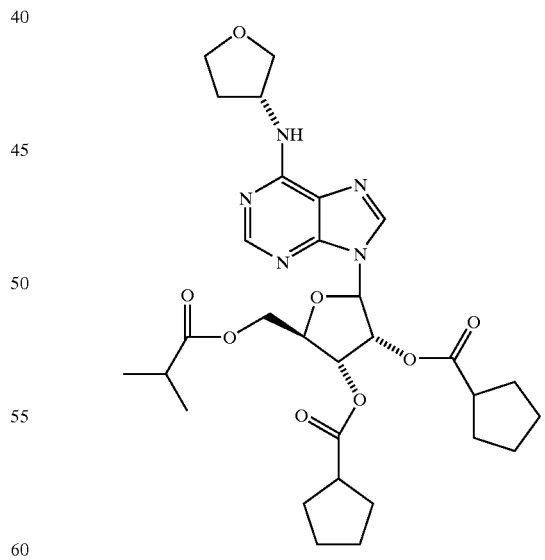

(5-{6-[((3R)oxolan-3-yl) amino]purin-9-yl}(2R, 3R, 4R)-3,4-diacetyloxyoxolan-2-yl)methyl 2-methylpropanoate (20).

Compound 20 was prepared in the manner of compound 15 utilizing isobutyric anhydride under conditions A for introduction of the ester group at the 5' hydroxyl group, and cyclopentanecarboxylic acid under conditions B for the introduction of the 2' and 3' hydroxyl groups: ¹H NMR (CDCl₃) δ1.15–1.18 (m, 611), 1.45–1.97 (m, 16H), 2.31–2.41 (m,1H), 2.55-2.79(m,2H), 3.75–3.87(m,2H), 3.95–4.01(m,2H), 4.37–4.42 (m, 3H), 5.61 (dd, 1H), 5.83 (dd, 1H), 6.15 (d, 1H), 7.92 (s,1H), 8.33(s,1H).

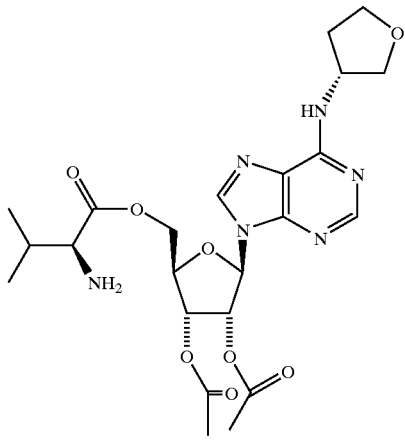

21

(5-{6-[((3R)oxolan-3-yl)amino]purin-9-yl}(2R, 3R, 4R)-3,4-diacetyloxyoxolan-2-yl)methyl (2S)-2-amino-3-methylbutanoate (21).

Compound 1 (1.0 g, 3 mmol) was first azeotroped with pyridine (3×10 mL), then dissolved in pyridine (20 mL). After cooling to 0 C., DMTCl (1.1 g, 3.3 mmol) was added in one portion. After 16 h the reaction was concentrated in vacuo, and the residue was dissolved in dichloromethane (100 mL), washed with 1% sodium bicarbonate (3×50 mL), and dried (sodium sulfate) to afford the mono DMT derivative 22 ¹H NMR(CDCl₃) δ1.9–2.0 (m,1H), 3.15–3.20(m, 2H), 3.55–3.60(m,1H), 3.65–3.75(m), 3.7(s)(7H), 3.8–3.9 (m,2H), 4.0–4.05(m,1H), 4.30(t, 1H), 4.60–4.7(m, 2H), 5.9 (d,1H), 6.8 (t, 4H), 7.1–7.25(m,7H), 7.3(d,2H), 8.15(s,1H), 8.25(s,1H).

To a solution of compound 22 (1.0 g, 1.56 mmol) and pyridine (20 mL) was added acetic anhydride (1 mL) and DMAP (100 mg). After 20 h at 23 C., the reaction was concentrated in vacuo. The residue was dissolved in dichloromethane (100 mL), washed with water (2×50 mL), and dried (sodium sulfate). Concentration in vacuo afforded compound 23 as a homogeneous material based on TLC that was used directly in the next reaction without further purification.

To a solution of compound 23 (1.0 g, 1.38 mmol) and dichloromethane (100 mL) was added 3% trichloroaectic acid:dichloromethane (100 mL) at 23 C. A bright red color was observed that coincided with loss of starting material (by TLC). After concentration in vacuo, the residue was purified by applying flash chromatography (methanol:dichloromethane, 1:9) to afford pure diacetate 24:¹H NMR (DMSO) δ1.8–2.2 (m), 1.95(s), 2.1(s)(8H), 3.55–3.65(m, 2H), 3.65–3.75(m, 2H), 3.8–3.95(m, 2H), 4.05–4.15(m, 1H), 4.2(d, 1H), 4.6–4.7(bs, 1H), 5.5(d, 1H), 5.9(dd, 1H), 6.2(d, 1H), 8.2(s, 1H), 8.4(s, 1H), 8.55(s, 1H).

Compound 24 (105 mg, 0.25 mmol), CBZ-Valine (125 mg, 0.5 mmol), DCC on PLC resin (400 mG) were shaken in dichloromethane (10 mL) overnight. The resin was filtered off, and the filtrate was concentrated in vacuo. The residue was purified by preparative TLC (methanol:dichloromethane, 1:9) to give 25: ¹H NMR (CDCl₃) δ0.85 (d,3H), 0.9(d, 3H), 1.9-2.2(m), 2.05(s),2.1(s)(8H), 2.3–2.4 (m, 1H), 3.75–3.9(m,2H), 3.95–4.0(m,2H), 4.3–4.5(m,4H), 4.8–4.9(bs,1H), 5.2(AB quartet center, 2H), 5.65(d,1H), 5.75(d,1H), 5.95(dd,1H), 6.1(d,1H), 6.35(d,1H), 7.2–7.3(m, 5H), 7.95(s, 1H), 8.4(s,1H).

Compound 25 (100 mg, 0.15 mmol), 10% Pd/C(100 mg), and anhydrous ethanol (10 mL) were submitted to a hydrogen atmosphere (5 psi) for 16 h. Removal of the catalyst through filtration, and concentration in vacuo afforded compound 21 as a pure product based on TLC and NMR: ¹H NMR(CD₃OD) δ1.0–1.1 (m,6H), 2.0–2.2(m), 2.1(s), 2.2(s) (7H), 2.25-2.35(m,1H), 2.35–2.5(m,1H), 3.8–4.2(m,4H), 4.5–4.8(m,4H), 5.6–5.7(m,1H), 5.95–6.05(m,1H), 6.3–6.4 (m,1H), 8.4–8.6(m,2H).

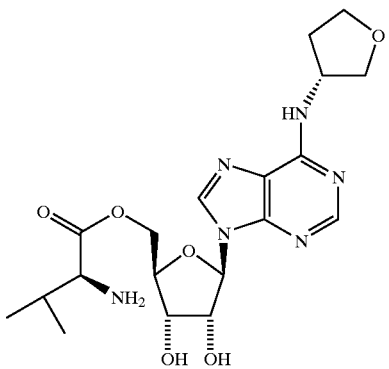

28

(5-{6-[((3R)oxolan-3-yl)amino]purin-9-yl}(2R, 3S, 4R)-3,4-dihydroxyoxolan-2-yl)methyl (2S)-2-amino-3-methylbutanoate (28).

Compound 15A (85 mg, 0.25 mmol), L-Valine(CBZ)(65 mgs, 0.25 mmol) DCC on PLC (Nova biochem, 300 mG) were shaken in dichloromethane (10 mL) overnight. After removing the resin through filtration, the reaction was concentrated in vacuo. The residue was purified by silica gel column chromatography (methanol:dichloromethane, 1:19) to afford 26 (100 mg, 77%):¹H NMR (CDCl₃) δ1.80(d,3H), 1.85(d,3H), 1.35(s,3H), 1.6(s,3H), 1.9-2.1(m,2H), 2.25–2.4 (m,1H), 3.7–3.9(m,2H), 3.9–4.05(m,2H), 4.2–4.5(m,4H), 5.0–5.1(m,3H), 5.5(d,1H), 5.75–5.85(m,1H), 6.4(bs,1H) 7.2–7.4(m,5H), 7.8(s,1H), 8.3(s,1H).

Compound 26 (100 mg, 0.16 mmol) was dissolved in 80% aq.acetic acid and heated at 80 C. for 5 h. After concentration in vacuo, the residue was purified by applying silica gel column chromatography (methanol:dichloromethane 1:9) to afford product 27 (50 mg, 54%).

Compound 27 (50 mg, 0.087 mmol), 10% Pd/C(100 mg) and anhydrous ethanol (10 mL) were submitted to a hydrogen atmosphere for 16 h. The catalyst was removed through filtration, and the filtrate concentrated under reduced pressure. The residue was purified by applying column chromatography (methanol:dichloromethane 1:4 to give pure product 28 (60 mg, 75%): ¹H NMR (CD₃OD) δ0.90(d,3H), 0.95(d,3H), 1.85–2.1(m,2H), 2.30–2.40(m,1H), 3.25–3.30 (m,2H), 3.70–3.80(m,1H), 3.80–3.90(m,1H), 3.95–4.05(t, 2H), 4.20–4.30(m,1H), 4.35-4.45(m,3H), 4.80(d,1H), 6.0(d, 1H), 8.2–8.3(m,2H).

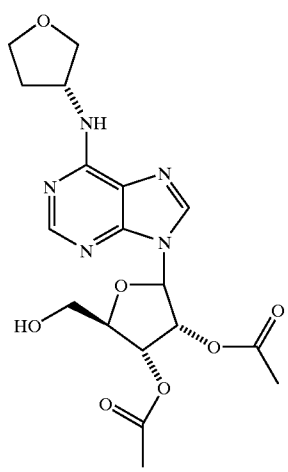

31

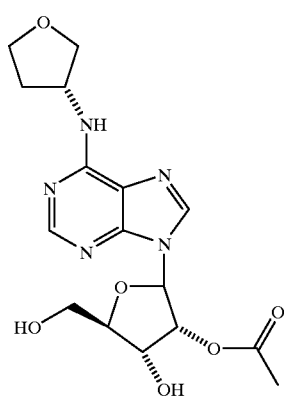

32

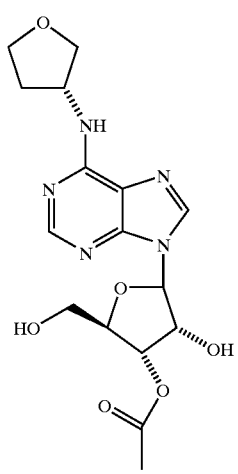

33

2-{6-[((3R)oxolan-3-yl)amino]purin-9-yl}(3R, 4R, 5R)-4-acetyloxy-5-(hydroxymethyl)oxolan-3-yl acetate (31).

To a solution of compound 22 (350 mg, 0.55 mmol) and pyridine (5 mL) was added acetic anhydride (55 µl, 1 eq). After 16 h at 23 C., the reaction was concentrated in vacuo. The residue was diluted with dichloromethane (100 mL), washed water (2×50 mL), and dried (sodium sulfate). Concentration in vacuo gave a mixture of products as shown by TLC. The NMR spectrum of this mixture indicated that it contained all three compounds 23, 29, 30. This crude mixture was used without purification in the next reaction.

To the mixture of 23, 29, and 30 (300 mG) and dicloromethane (100 mL) was added 3% trichloroacetic acid (100 mL) at 23 C. A bright red color was observed that coincided with the disappearance of starting material by TLC, After concentration in vacuo, the residue was applied to preparative TLC (methanol:methylene chloride 1:10) to afford compound 31 and a mixture of compounds 32 and 33 (1:2 ratio): Compound 31: $^1$H NMR(CD$_3$OD) 62.0-2.1(m,1H), 2.1(s), 2.15(s, 3H), 2.3–2.4(m,1H), 3.7–3.8(m, 2H), 3.8–3.9 (m, 2H), 3.95–4.05(m, 2H), 4.1–4.15(m), 4.25–4.3(m)(1H), 4.7–4.8(m,1H), 4.9–5.0(m,1H), 5.4 (d, 1H), 5.6(t, 1H), 5.9 (d, 1H),6.2(d, 1H), 8.2–8.3(m,2H).

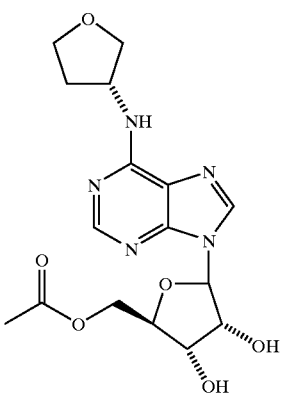

(5-{6-[((3R)oxolan-3-yl)amino]purin-9-yl}(3S, 2R, 4R)-3,4-dihydroxyoxolan-2-yl)methyl acetate (34).

Compound 34 was prepared from intermediate 15B by deprotecting the 2' and 3' hydroxyl groups using 4N HCl in dioxane in the manner of compound 15C: $^1$H NMR (CDOD$_3$) δ1.85–2.03(m,1H), 1.98 (s, 3H), 2.22–2.34(m, 1H), 3.71–3.81(m, 2H), 3.83-3.95 (m, 2H), 4.23–4.35(m, 3H), 4.53–4.62 (m, 1H), 4.65–4.78 (m,1H), 5.93–5.99(m, 1H),6.68–6.80(m, 1H), 7.93 (br s, 1H), 8.15 (m,1H).

EXAMPLE 5

Adult male and female Sprague Dawley rats were implanted with transducer/emitter modules of the Data Science Telemetry system (St. Paul, Minn.) to allow continuous monitoring of heart rate (HR). At the start of the experiment, basal HR was determine for 1 hour prior to gavage. A 500 µg dose of compounds prepared according to Examples 1–4 was administered to by oral gavage. The compounds were each prepared as stock solutions in DMSO and diluted at least 1:1000 in water for gavage. Following administration, HR was determined every five minutes. In these experiments, 3–6 rats were used to test each compounds. An average of the HR results are reported in Table 1, below and in FIGS. 1A, 2A, 3A and 4A.

TABLE 1

Effect on Rat Heart Rate After Oral Gavage - 500 µGram Dose.

| Compound Number | Effect on Heart Rate | N |
|---|---|---|
| 2 | +++ | 4 |
| 8 | +++ | 4 |
| 19 | +++ | 3 |
| 15 | +++ | 3 |
| 9 | ++ | 4 |

TABLE 1-continued

Effect on Rat Heart Rate After Oral Gavage - 500 μGram Dose.

| Compound Number | Effect on Heart Rate | N |
|---|---|---|
| 6 | ++ | 4 |
| 7 | + | 4 |
| 4 | + | 4 |
| 10 | + | 4 |
| 14 | + | 4 |
| 18 | + | 3 |
| 16 | + | 3 |
| 21 | + | 3 |
| 31 | +/− | 4 |
| 5 | +/− | 4 |
| 12 | − | 4 |
| 11 | − | 4 |
| 13 | − | 4 |
| 17 | − | 3 |
| 20 | − | 3 |
| 34 | − | 3 |
| 32 and 33 | − | 3 |
| 28 | − | 3 |

+++ = Heart Rate decreased by 100–150 BPM
++ = Heart Rate decreased by 50–100 BPM
+ = Heart rate decreased by 50 BPM
=/− = No reproducible effect on Heart Rate.
− = No effect on Heart Rate.

Compound 1, identified above is an $A_1$ Agonist. Compound 1 is administered IP (0.025 mg), it lowers the heart rate of the sinus rhythm of the rat. Thus, this in vivo assay is a measure of effect on heart rate following the oral administration of a pro-drug of a potent adenosine A1 agonist. The plasma concentrations of compound 1 was determined over time by cannulating the jugular of a separate specimen for subsequent blood collection. After a 24 hour recovery period, a pre-dose baseline HR as determined followed by gavage or IP injection of a compound being tested. Blood samples were taken and the concentration of compound 1 in the plasma was determined using LC/MS/MS methodologies. The plasma concentrations of compound 1 following dosing of a selected compound are reported in FIGS. 1A, 2A, 3A and 4A.

Figure 1B:
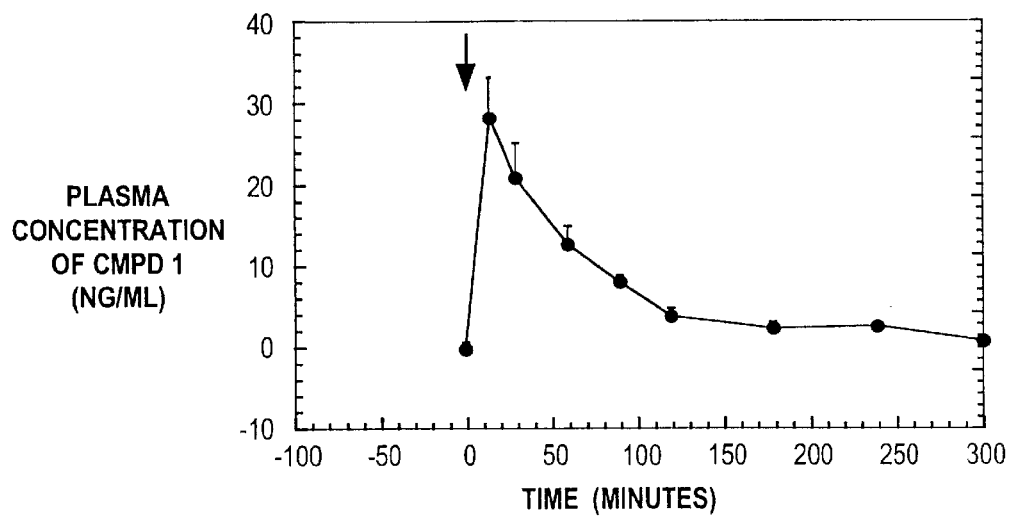
FIG. 1B is a plot of the plasma concentration of compound 1 over time beginning just prior to administration of compound 2 by oral gavage.

Compound 2 of Example 1, a 2',3', 5'-triacetoxy derivative, was administered to 4 rats in an oral gavage at a dose of 0.5 mg/kg. FIG. 1A is a plot of the rat HR prior to and after administration of compound 2 The arrow on the graph indicates the time of dosing of compound 2. It is apparent that a rapid onset of the drug was observed based on the decrease in heart rate which was between 100–150 beats per minute and based upon plasma compound 1 levels reported in FIG. 1B. Compound 2 is a pro-drug that is converted to the active moiety in plasma. In 4 different rats, the plasma level of compound 1 was determined following oral dosing at 0.5 mg/kg of compound 2. There is a good correspondence between the conversion to the active moiety compound 1 and the activity observed in FIG. 1B. There may be intermediates that are contributing to the activity (ie. mono acetoxy or diacetoxy derivatives of compound 2), and these are meant to be part of this invention. Compound 1 has been shown to be a potent adenosine A1 agonist in U.S. Pat. No. 5,789,416.

Figure 2A:
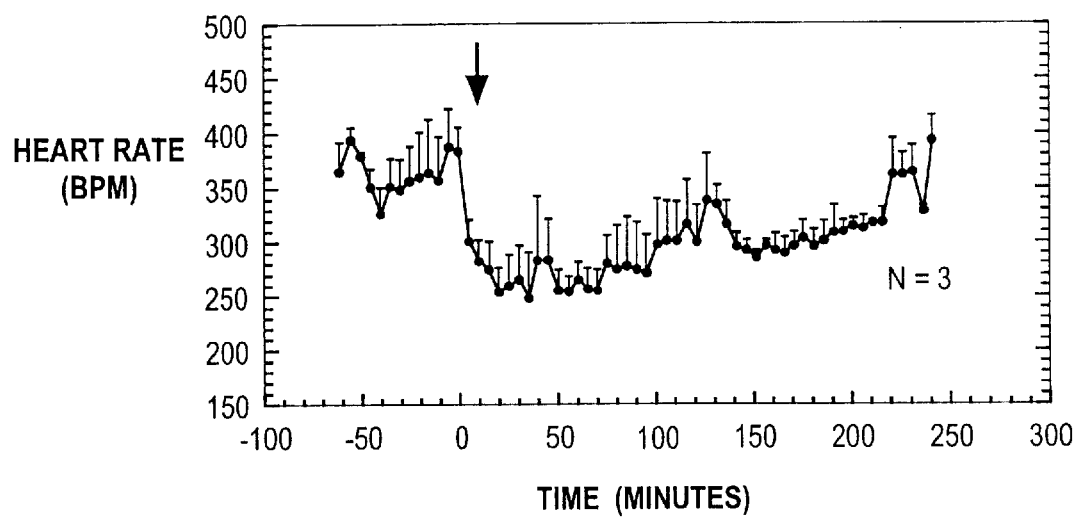
FIG. 2A is a plot of heart rate over time prior to and following administration of compound 8 of Example 2 to 4 rats in an oral gavage at a dose of 0.5 mg/kg.
Figure 2B:
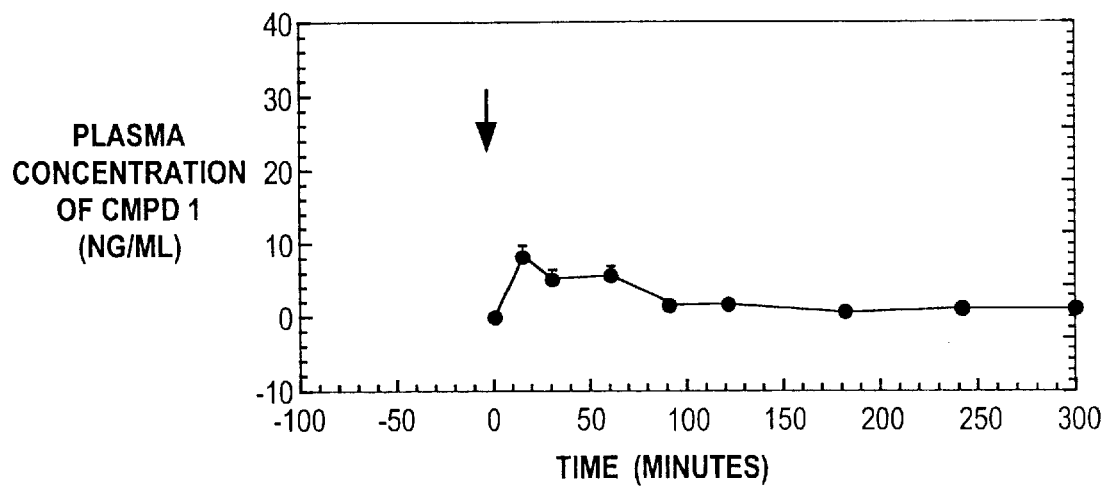
FIG. 2B is a plot of the plasma concentration of compound 1 over time beginning just prior to administration of compound 8 by oral gavage.

Compound 8 of Example 2, a 2',3', 5'-triscyclopentylcarboxyl derivative, was administered to 3 rats in an oral gavage at a dose of 0.5 mg/kg. FIG. 2A is a plot of the rat HR prior to and after administration of compound 8. The arrow on the graph indicates the time of dosing of compound 8. It is apparent that a rapid onset of the drug was observed based on the decrease in heart rate which was between 100–150 beats per minute. Compound 8 is a pro-drug that is converted to the active moiety in plasma, compound 1. In 4 different rats, the plasma level of compound 1 was determined following oral dosing at 0.5 mg/kg of compound 8. The levels are plotted against time in FIG. 2B. There is a correspondence between the conversion to the active moiety compound 1 and the activity observed. There may be intermediates that are contributing to the activity (ie. mono cyclopentylcarboxyl or dicyclopentylcarboxyl derivatives of compound 8), and these are part of this invention.

Figure 3A:
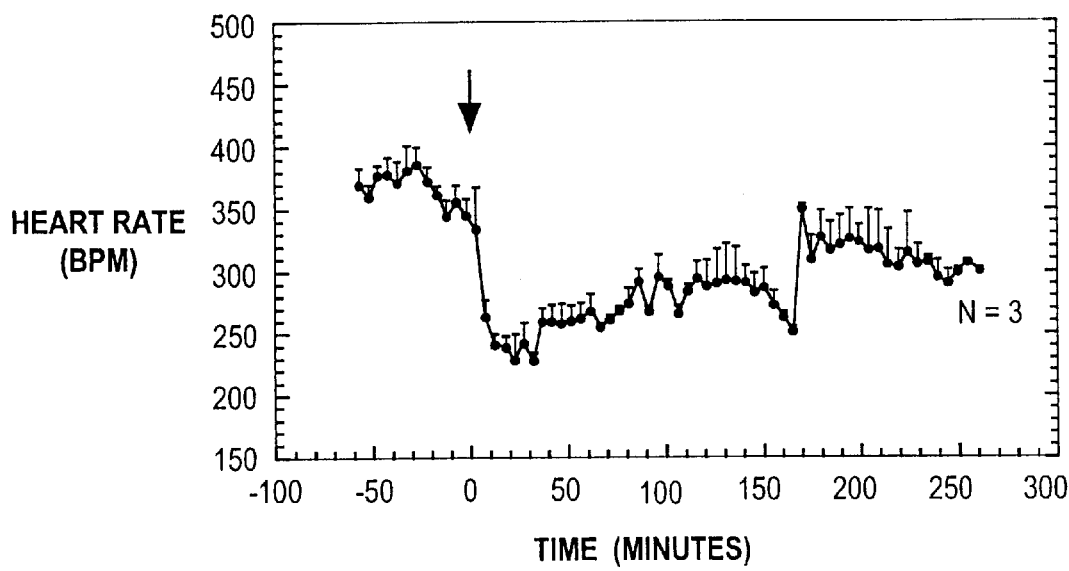
FIG. 3A is a plot of heart rate over time prior to and following administration of compound 15 of Example 4 to 4 rats in an oral gavage at a dose of 0.5 mg/kg.
Figure 3B:
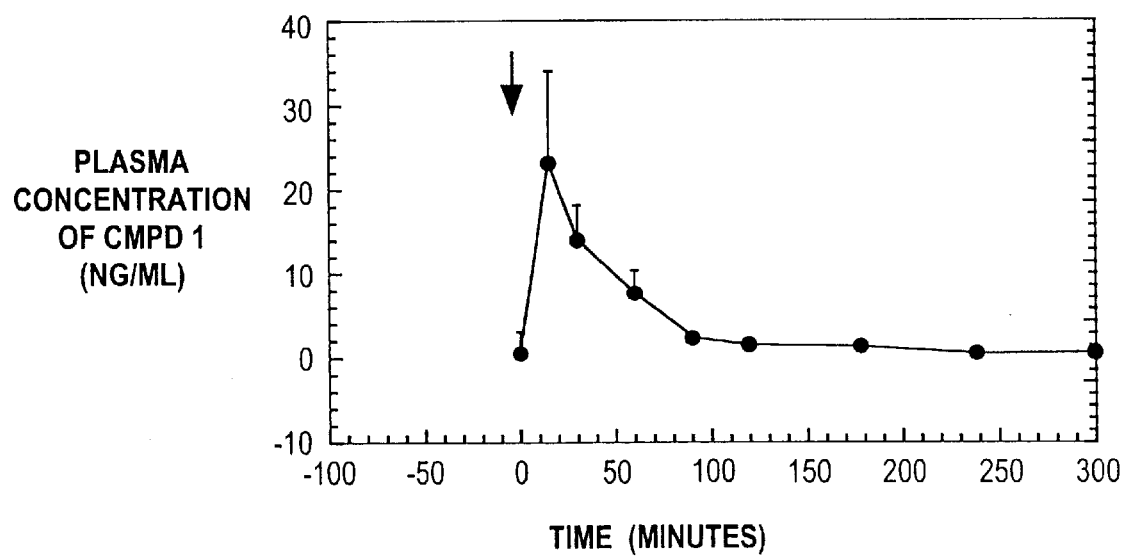
FIG. 3B is a plot of the plasma concentration of compound 1 over time beginning just prior to administration of compound 15 by oral gavage.

Compound 15 of Example 4, a 2',3'-bisisobutyryl-5'-acetoxy derivative, was administered to 3 rats in an oral gavage at a dose of 0.5 mg/kg. FIG. 3A is a plot of the rat HR prior to and after administration of compound 15. The arrow on the graph indicates the time of dosing of compound 15. It is apparent that a rapid onset of the drug was observed based on the decrease in heart rate which was between 100–150 beats per minute. Compound 15 is a pro-drug that is converted to the active compound 1 moiety in plasma. In 4 different rats, the plasma level of compound 1 was determined following oral dosing at 0.5 mg/kg of compound 15. The plasma compound 1 levels are plotted against time in FIG. 3B. There is a correspondence between the conversion to the active moiety compound 1 and the activity observed in FIG. 3B. There may be intermediates that are contributing to the activity (ie. mono isobutyryl, mono acetoxy derivatives, or diester combinations of compound 15), and these are meant to be part of this invention.

Figure 4A:
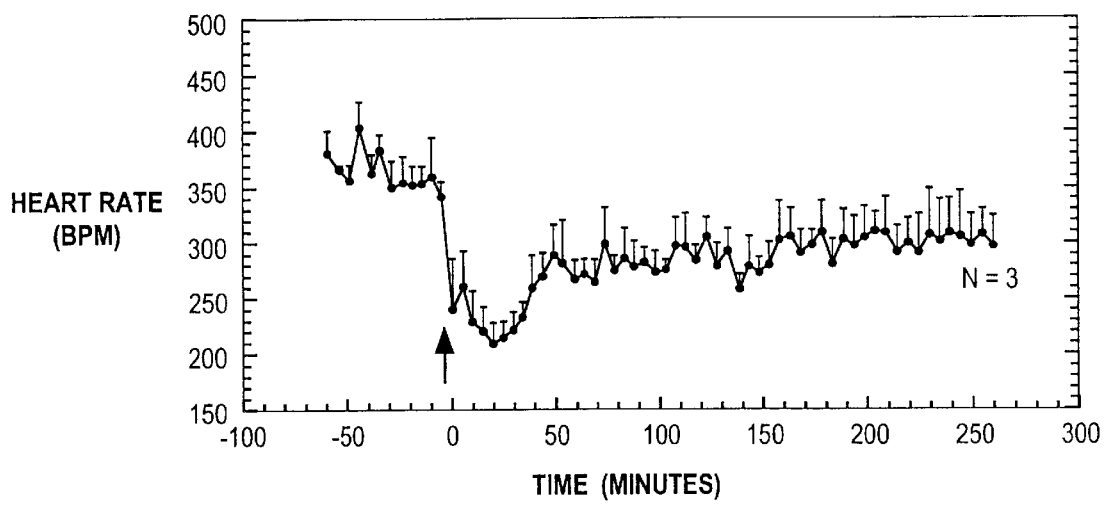
FIG. 4A is a plot of heart rate over time prior to and following administration of compound 19 of Example 4 to 4 rats in an oral gavage at a dose of 0.5 mg/kg.
Figure 4B:
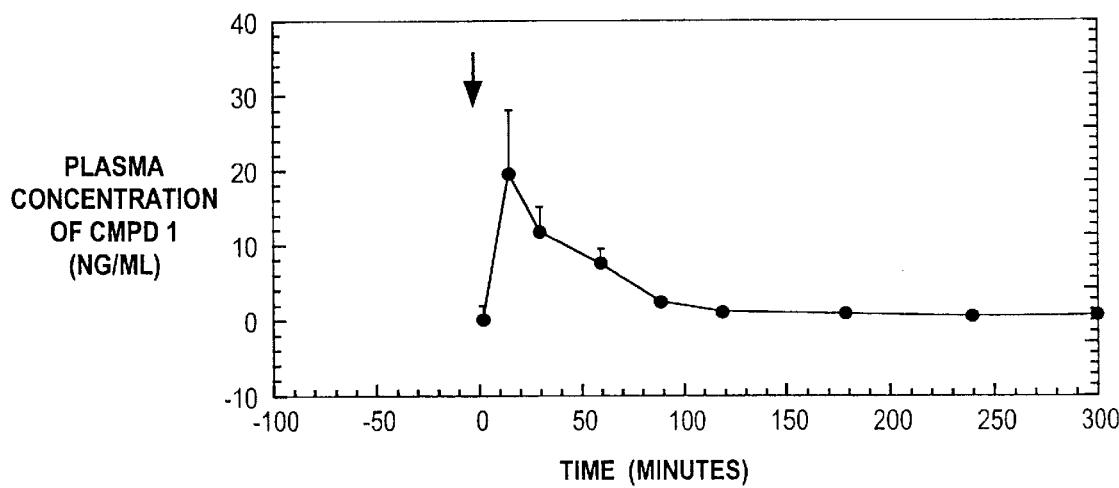
FIG. 4B is a plot of the plasma concentration of compound 1 over time beginning just prior to administration of compound 19 by oral gavage.

Compound 19 of Example 4, a 2',3'-diacetoxy-5'-isobutyryl derivative, was administered to 3 rats in an oral gavage at a dose of 0.5 mg/kg. FIG. 4A is a plot of the rat HR prior to and after administration of compound 19. The arrow on the graph indicates the time of dosing of compound 19. It is apparent that a rapid onset of the drug was observed based on the decrease in heart rate which was between 100–150 beats per minute. Compound 19 is a pro-drug that is converted to the active moiety in plasma, compound 1. In 4 different rats, the plasma level of compound 1 was determined following oral dosing at 0.5 mg/kg of compound 19. The plasma levels of compound are plotted against time in FIG. 4B. There is a correspondence between the conversion to the active moiety compound 1 and the activity observed in FIG. 4B. There may be intermediates that are contributing to the activity (ie. mono isobutyryl, mono acetoxy derivatives, or diester combinations of compound 19), and these are meant to be part of this invention.

Figure 5:
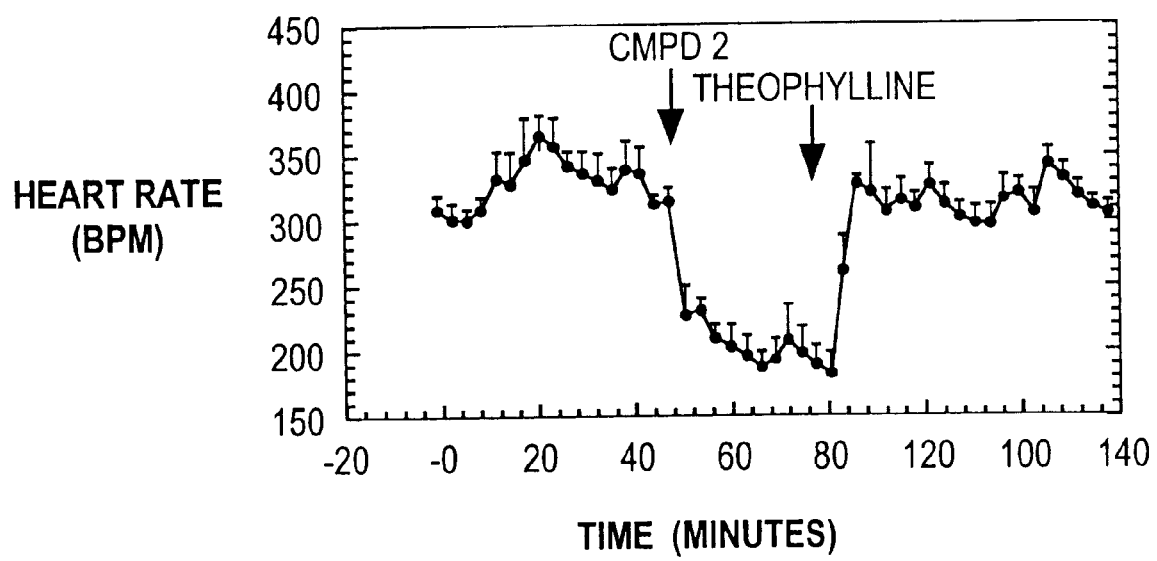
FIG. 5 is a plot of heart rate over time prior to and following administration of compound 2 of Example 1 to 4 rats in an oral gavage at a dose of 0.5 mg/kg and thereafter administering theophylline at a dose of 7.5 mg/kg.

Compound 2 prepared in Example 1, a 2',3',5'-triacetoxy derivative, was administered to 4 rats in an oral gavage at a dose of 0.5 mg/kg. FIG. 5 is a plot of the rat HR prior to and after administration of compound 8. The arrow on the graph indicates the time of dosing of compound 2. It is apparent that a rapid onset of the drug was observed based on the decrease in heart rate which was between 100–150 beats per minute. The effect on heart rate following oral administration of compound 2 was reversible by administering theophylline at a dose of 7.5 mg/kg. Theophylline is a non specific antagonist of all of the adenosine receptor subtypes A1, A2, and A3. Thus, this data supports that the effect on heart rate following oral administration of compound 2 is mediated by adenosine receptors.

What we claim is:

1. A compound having the formula:

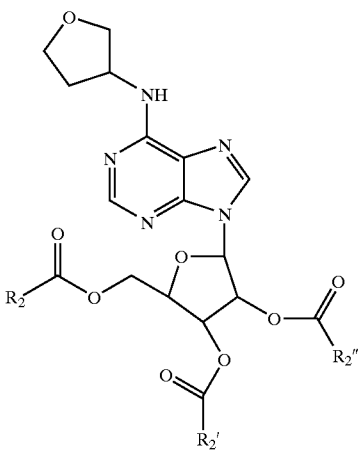

wherein $R_2$, $R_2'$, and $R_2''$ are independently selected from the group of $C_{1-5}$ alkyl, $C_{3-6}$ cycloalkyl, and 2-, 3-, 4-pyridinyl, which alkyl, cycloalkyl, and pyridinyl are optionally substituted with 1 to 3 substituents independently selected from the group consisting of $OR^{20}$ and $N(R^{20})_2$; and $R^{20}$ is selected from the group consisting of hydrogen and $C_{1-5}$ alkyl, which alkyl group is optionally substituted with 1 to 3 phenyl groups.

2. The compound of claim 1 wherein $R_2$, $R_2'$, and $R_2''$ are independently $C_{1-5}$ alkyl, which alkyl is optionally substituted with 1 to 3 substituents independently selected from the group consisting of $OR^{20}$ and $N(R^{20})_2$; and $R^{20}$ is selected from the group consisting of hydrogen and $C_{1-5}$ alkyl, which alkyl group is optionally substituted with 1 to 3 phenyl groups.

3. The compound of claim 2 wherein $R_2$, $R_2'$, and $R_2''$ are independently $C_{1-5}$ alkyl, which alkyl is optionally substituted with 1 to 3 $N(R^{20})_2$ groups; and $R^{20}$ is selected from the group consisting of hydrogen and $C_{1-5}$ alkyl, which alkyl group is optionally substituted with 1 to 3 phenyl groups.

4. The compound of claim 3 wherein $R_2$, $R_2'$, and $R_2''$ are independently $C_{1-5}$ alkyl, which alkyl is optionally substituted with 1 $N(R^{20})_2$ groups; and $R^{20}$ is selected from the group consisting of hydrogen and $C_{1-5}$ alkyl, which alkyl group is optionally substituted with 1 to 3 phenyl groups.

5. The compound of claim 4 wherein $R_2$, $R_2'$, and $R_2''$ are independently $C_{1-5}$ alkyl, which alkyl is optionally substituted with 1 $N(R^{20})_2$ groups; and $R^{20}$ is hydrogen.

6. The compound of claim 2 wherein $R_2$, $R_2'$, and $R_2''$ are independently $C_{1-5}$ alkyl, which alkyl is optionally substituted with 1 to 3 $OR^{20}$ groups; and $R^{20}$ is selected from the group consisting of hydrogen and $C_{1-5}$ alkyl, which alkyl group is optionally substituted with 1 to 3 phenyl groups.

7. The compound of claim 6 wherein $R_2$, $R_2'$, and $R_2''$ are independently $C_{1-5}$ alkyl, which alkyl is optionally substituted with 1 to 3 $OR^{20}$ groups; and $R^{20}$ is $C_{1-5}$ alkyl.

8. The compound of claim 7 wherein $R_2$, $R_2'$, and $R_2''$ are independently $C_{1-5}$ alkyl, which alkyl is optionally substituted with 1 $OR^{20}$ group; and $R^{20}$ is $C_{1-5}$ alkyl.

9. The compound of claim 8 wherein $R_2$, $R_2'$, and $R_2''$ are independently $C_{1-5}$ alkyl.

10. The compound of claim 9 wherein $R_2$, $R_2'$, and $R_2''$ are each methyl.

11. The compound of claim 1 wherein $R_2$, $R_2'$, and $R_2''$ are independently selected from the group consisting of $C_{1-5}$ alkyl and $C_{3-6}$ cycloalkyl.

12. The compound of claim 11 wherein all 3 of $R_2$, $R_2'$, and $R_2''$ are independently $C_{3-6}$ cycloalkyl.

13. The compound of claim 11 wherein 2 of $R_2$, $R_2'$, and $R_2''$ are independently $C_{3-6}$ cycloalkyl and 1 of $R_2$, $R_2'$, and $R_2''$ is $C_{1-5}$ alkyl.

14. The compound of claim 11 wherein 1 of $R_2$, $R_2'$, and $R_2''$ is $C_{3-6}$ cycloalkyl and 1 of $R_2$, $R_2'$, and 2 of $R_2''$ are independently $C_{1-5}$ alkyl.

15. The compound of claim 1 wherein $R_2$, $R_2'$, and $R_2''$ are independently 2-, 3-, or 4-pyridinyl.

16. A method for treating a mammal experiencing a coronary electrical disorder normally treatable by administration of adenosine or an $A_1$ adenosine receptor agonist comprising administering a therapeutically effective amount of a compound of claim 1 to the mammal.

17. The method of claim 16 wherein the therapeutically effective amount ranges from about 0.01 to about 100 mg/kg weight of the mammal.

18. The method of claim 16 wherein the compound is administered to a mammal experiencing a coronary electrical disorder selected from the group consisting of supraventricular tachycardias, atrial fibrillation, atrial flutter, and AV nodal re-entrant tachycardia.

19. The method of claim 16 wherein the mammal is a human.

20. A pharmaceutical composition comprising a compound of claim 1 combination with a pharmaceutically acceptable carrier or excipient.

21. The pharmaceutical composition of claim 20 wherein the pharmaceutical composition is in the form of a solution.

22. The pharmaceutical composition of claim 20 wherein the pharmaceutical composition is in the form of a tablet.

* * * * *